US010676741B2

(12) United States Patent
Ding et al.

(10) Patent No.: US 10,676,741 B2
(45) Date of Patent: Jun. 9, 2020

(54) NUCLEOTIDE SEQUENCE AND METHOD FOR CONTROLLING INSECT INFESTATION

(71) Applicant: BEIJING DABEINONG BIOTECHNOLOGY CO., LTD., Beijing (CN)

(72) Inventors: Derong Ding, Beijing (CN); Aihong Zhang, Beijing (CN)

(73) Assignee: BEIJING DABEINONG BIOTECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/068,090

(22) PCT Filed: Dec. 9, 2016

(86) PCT No.: PCT/CN2016/109177
§ 371 (c)(1),
(2) Date: Jul. 3, 2018

(87) PCT Pub. No.: WO2017/118260
PCT Pub. Date: Jul. 13, 2017

(65) Prior Publication Data
US 2019/0367912 A1 Dec. 5, 2019

(30) Foreign Application Priority Data
Jan. 4, 2016 (CN) .......................... 2016 1 0004410

(51) Int. Cl.
*C12N 15/82* (2006.01)
*C12N 15/113* (2010.01)
*A01N 57/16* (2006.01)

(52) U.S. Cl.
CPC ............ *C12N 15/113* (2013.01); *A01N 57/16* (2013.01); *C12N 15/8218* (2013.01); *C12N 15/8286* (2013.01); *C12N 2310/14* (2013.01)

(58) Field of Classification Search
None
See application file for complete search history.

(56) References Cited

U.S. PATENT DOCUMENTS

| 7,812,219 B2 * | 10/2010 | Baum ................. | C12N 15/8286 800/279 |
| 2008/0214443 A1 | 9/2008 | Baum et al. | |
| 2013/0291188 A1 * | 10/2013 | Bogaert ............... | C12N 15/113 800/265 |

FOREIGN PATENT DOCUMENTS

| CN | 101370941 A | | 2/2009 |
| CN | 101686705 | | 11/2013 |
| CN | 103993079 A | | 8/2014 |
| CN | 104987376 | | 10/2015 |
| WO | 2008134072 A2 | | 11/2008 |
| WO | 2010025320 | | 3/2010 |
| WO | WO 2011082217 | * | 7/2011 |
| WO | 2017118260 | | 7/2017 |

OTHER PUBLICATIONS

Christiaens et al., "The challenge of RNAi-mediated control of hemipterans", Current Opinion in Insect Science 2014; 6:15-21.
Lu et al., "Knock down of *Nilaparvata lugens* Genes through dsRNA Feeding on Artificial Diet and Transgenic Plants", Journal of Agricultural Biotechnology, 2013, 21(9): 1028-1036.
Predicted: Trichogramma pretiosum charged multivesicular body protein 4b (LOC106658336), mRNA, 2018, https://www.ncbi.nlm.nih.gov/nuccore/XM_014380235.
First Office Action dated Jan. 8, 2018 for Chinese Application No. 201610004410.2.
Second Office Action dated Jul. 25, 2018 for Chinese Application No. 201610004410.2.
Waker III et al., "RNA interference-mediated knockdown of IAP in Lygus lineolaris induces mortality in adult and pre-adult life stages", Entomologia Experimentalis et Applicata, 2011, 138: 83-92.
Zhou et al., "Silencing in Apolygus lucorum of the olfactory coreceptor *Orco* gene by RNA interference induces EAG response declining to two putative semiochemicals", Journal of Insect Physiology, 2014, 60: 31-39.

* cited by examiner

*Primary Examiner* — Medina A Ibrahim
(74) *Attorney, Agent, or Firm* — James S. Keddie; Bozicevic, Field & Francis LLP

(57) ABSTRACT

Disclosed are a nucleotide sequence and a method for controlling insect invasions, the isolated polynucleotide sequence comprising: (a) a polynucleotide sequence as shown in SEQ ID NO: 1, 2 or 3; or (b) a polynucleotide sequence hybridizing with the polynucleotide sequence defined in (a) under stringent conditions; or (c) a polynucleotide sequence having an identity of not less than 80% to the polynucleotide sequence defined in (a); or (d) a polynucleotide sequence of at least 19 consecutive nucleotides of the polynucleotide sequence defined in (a), wherein a double-stranded RNA comprising at least one strand complementary to the polynucleotide sequence, when ingested by an insect pest from *Hemiptera*, inhibits growth of the insect pest; or (e) a complementary sequence of the polynucleotide sequence as defined in (a), (b), (c) or (d). The three target sequences for controlling an insect pest from *Hemiptera, Lygus*, have the advantages of efficiency, specificity, convenience and low cost.

17 Claims, 1 Drawing Sheet
Specification includes a Sequence Listing.

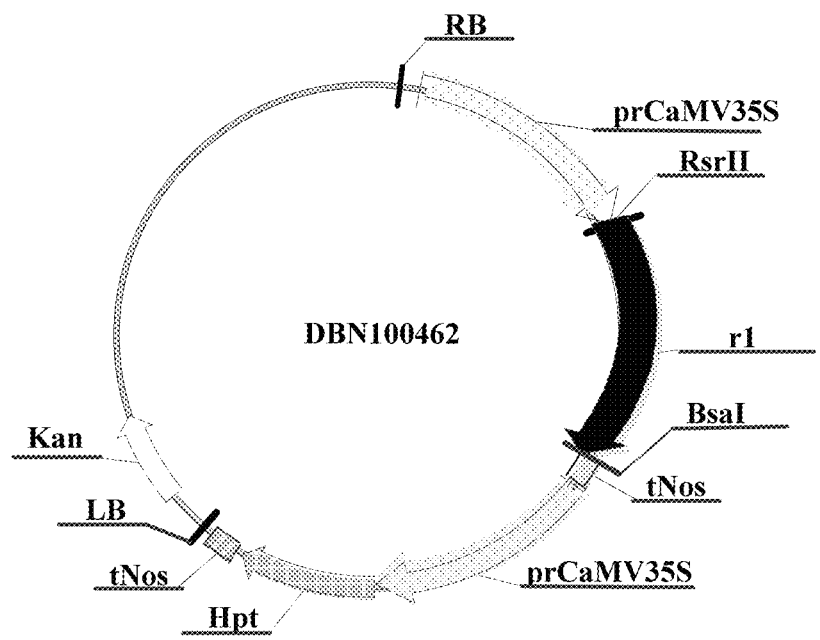

ND METHOD FOR CONTROLLING INSECT INFESTATION

SEQUENCE LISTING

<160> NUMBER OF SEQ ID NOS: 18

<210> SEQ ID NO 1
<211> LENGTH: 240
<212> TYPE: DNA
<213> ORGANISM: Apolygus lucorum

<400> SEQUENCE: 1

| aagcaaatag tagtagacca aaccgtcaaa atccctaagg gattgacgtg caccgtcaaa | 60 |
| tccaggatcg tcacgatcaa gggaccgaga ggcaccctga agaggacctt cagacatttg | 120 |
| gccctcgaca tctccatggt gaaccccaga gtacttaaag tggaaaagtg gttcggtacc | 180 |
| aagaaagaac tcgccgcagt cagaactgtg tgctcccaca tcgagaacat gatcaaagga | 240 |

<210> SEQ ID NO 2
<211> LENGTH: 332
<212> TYPE: DNA
<213> ORGANISM: Apolygus lucorum

<400> SEQUENCE: 2

| ttgaagccga aatgatgatc atcaagaaga atggcacggc aaataggcgt gtatctattc | 60 |
| aagctctaaa gaagaagaag cgttttgaaa agcaacttca gcagattgat ggaactctat | 120 |
| cgacaattga aatgcagaga gaagccttgg aatcagctaa tactagttcc aaggttgtac | 180 |
| aaactatgaa attagccgct gatacactga agactgctca tcagcacatg gatgttgatc | 240 |
| aagttcacga catgatggat gaaattgctg aacagcatga agcagcgaag gaaatatcag | 300 |
| atgccatatc aaacccggtt gcctttggaa ac | 332 |

<210> SEQ ID NO 3
<211> LENGTH: 221
<212> TYPE: DNA
<213> ORGANISM: Apolygus lucorum

<400> SEQUENCE: 3

| gtcacgctcc gcatcagaga caaggaccaa gacctcgtca acaacctcgt tcccgtgatc | 60 |
| caggacaagt acaaggaaat ctccggtctc gaaattaagc tcaaaatcga caccgagtct | 120 |
| ttcctccctc ccgactccag cggcggtatc gaactcctag ctctcaaaaa ccgcatcaag | 180 |
| gtgtccaaca ctctcgagag ccgtctcgac ttgatcgctc a | 221 |

<210> SEQ ID NO 4
<211> LENGTH: 578
<212> TYPE: DNA
<213> ORGANISM: Artificial Sequence
<220> FEATURE:
<223> OTHER INFORMATION: r1 Nucleotide sequence

<400> SEQUENCE: 4

| aagcaaatag tagtagacca aaccgtcaaa atccctaagg gattgacgtg caccgtcaaa | 60 |
| tccaggatcg tcacgatcaa gggaccgaga ggcaccctga agaggacctt cagacatttg | 120 |
| gccctcgaca tctccatggt gaaccccaga gtacttaaag tggaaaagtg gttcggtacc | 180 |
| aagaaagaac tcgccgcagt cagaactgtg tgctcccaca tcgagaacat gatcaaagga | 240 |
| aagtactgcg atcgcgttaa cgctgtgatg tgaaacttga aattatttgt gttttgattg | 300 |
| tgattgtgag agtaacggtg gcggccgcct gcaggagctc ctttgatcat gttctcgatg | 360 |
| tgggagcaca cagttctgac tgcggcgagt tctttcttgg taccgaacca cttttccact | 420 |
| ttaagtactc tggggttcac catggagatg tcgagggcca aatgtctgaa ggtcctcttc | 480 |

```
agggtgcctc tcggtccctt gatcgtgacg atcctggatt tgacggtgca cgtcaatccc      540
ttagggattt tgacggtttg gtctactact atttgctt                              578

<210> SEQ ID NO 5
<211> LENGTH: 762
<212> TYPE: DNA
<213> ORGANISM: Artificial Sequence
<220> FEATURE:
<223> OTHER INFORMATION: r2 Nucleotide sequence

<400> SEQUENCE: 5
ttgaagccga aatgatgatc atcaagaaga atggcacggc aaataggcgt gtatctattc       60
aagctctaaa gaagaagaag cgttttgaaa agcaacttca gcagattgat ggaactctat      120
cgacaattga aatgcagaga gaagccttgg aatcagctaa tactagttcc aaggttgtac      180
aaactatgaa attagccgct gatacactga agactgctca tcagcacatg gatgttgatc      240
aagttcacga catgatggat gaaattgctg aacagcatga agcagcgaag gaaatatcag      300
atgccatatc aaacccggtt gcctttggaa acaagtactg cgatcgcgtt aacgctgtga      360
tgtgaaactt gaaattattt gtgttttgat tgtgattgtg agagtaacgg tggcggccgc      420
ctgcaggagc gtttccaaag gcaaccgggt tgatatggc atctgatatt ccttcgctg       480 cttcatgctg ttcagcaatt tcatccatca tgtcgtgaac ttgatcaaca tccatgtgct      540
gatgagcagt cttcagtgta tcagcggcta atttcatagt ttgtacaacc ttggaactag      600
tattagctga ttccaaggct tctctctgca tttcaattgt cgatagagtt ccatcaatct      660
gctgaagttg cttttcaaaa cgcttcttct tctttagagc ttgaatagat acacgcctat      720
ttgccgtgcc attcttcttg atgatcatca tttcggcttc aa                         762

<210> SEQ ID NO 6
<211> LENGTH: 540
<212> TYPE: DNA
<213> ORGANISM: Artificial Sequence
<220> FEATURE:
<223> OTHER INFORMATION: r3 Nucleotide sequence

<400> SEQUENCE: 6
gtcacgctcc gcatcagaga caaggaccaa gacctcgtca acaacctcgt tcccgtgatc       60
caggacaagt acaaggaaat ctccggtctc gaaattaagc tcaaaatcga caccgagtct      120
ttcctccctc ccgactccag cggcggtatc gaactcctag ctctcaaaaa ccgcatcaag      180
gtgtccaaca ctctcgagag ccgtctcgac ttgatcgctc aaagtactgc gatcgcgtta      240
acgctgtgat gtgaaacttg aaattatttg tgttttgatt gtgattgtga gagtaacggt      300
ggcggccgcc tgcaggagct gagcgatcaa gtcgagacgg ctctcgagag tgttggacac      360
cttgatgcgg ttttttgagag ctaggagttc gataccgccg ctggagtcgg agggaggaa      420 agactcggtg tcgattttga gcttaatttc gagaccggag atttccttgt acttgtcctg      480
gatcacggga acgaggttgt tgacgaggtc ttggtccttg tctctgatgc ggagcgtgac      540

<210> SEQ ID NO 7
<211> LENGTH: 328
<212> TYPE: DNA
<213> ORGANISM: Cauliflower mosaic virus

<400> SEQUENCE: 7
ccattgccca gctatctgtc actttattgt gaagatagtg gaaaggaag gtggctccta       60
```

```
caaatgccat cattgcgata aaggaaaggc catcgttgaa gatgcctctg ccgacagtgg      120
tcccaaagat ggaccccac ccacgaggag catcgtggaa aaagaagacg ttccaaccac       180
gtcttcaaag caagtggatt gatgtgatat ctccactgac gtaagggatg acgcacaatc     240
ccactatcct tcgcaagacc cttcctctat ataaggaagt tcatttcatt tggagaggac     300
acgctgacaa gctgactcta gcagatct                                        328
```

<210> SEQ ID NO 8
<211> LENGTH: 253
<212> TYPE: DNA
<213> ORGANISM: Agrobacterium tumefaciens

<400> SEQUENCE: 8

```
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggttttttatg attagagtcc cgcaattata catttaatac    180
gcgatagaaa acaaaatata gcgcgcaaac taggataaat tatcgcgcgc ggtgtcatct     240
atgttactag atc                                                        253
```

<210> SEQ ID NO 9
<211> LENGTH: 1026
<212> TYPE: DNA
<213> ORGANISM: Salmonella enterica

<400> SEQUENCE: 9

```
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat    180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat    360
gcgatcgctg cggccgatct tagccagacg agcgggttcg cccattcgg accgcaagga    420 atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

<210> SEQ ID NO 10
<211> LENGTH: 20
<212> TYPE: DNA
<213> ORGANISM: Artificial Sequence
<220> FEATURE:
<223> OTHER INFORMATION: Primer 1

<400> SEQUENCE: 10
cagggtgtca cgttgcaaga                                          20

<210> SEQ ID NO 11
<211> LENGTH: 20
<212> TYPE: DNA
<213> ORGANISM: Artificial Sequence
<220> FEATURE:
<223> OTHER INFORMATION: Primer 2

<400> SEQUENCE: 11
ccgctcgtct ggctaagatc                                          20

<210> SEQ ID NO 12
<211> LENGTH: 24
<212> TYPE: DNA
<213> ORGANISM: Artificial Sequence
<220> FEATURE:
<223> OTHER INFORMATION: Probe 1

<400> SEQUENCE: 12
tgcctgaaac cgaactgccc gctg                                     24

<210> SEQ ID NO 13
<211> LENGTH: 18
<212> TYPE: DNA
<213> ORGANISM: Artificial Sequence
<220> FEATURE:
<223> OTHER INFORMATION: Target sequence 1-F

<400> SEQUENCE: 13
aagcaaatag tagtagac                                            18

<210> SEQ ID NO 14
<211> LENGTH: 18
<212> TYPE: DNA
<213> ORGANISM: Artificial Sequence
<220> FEATURE:
<223> OTHER INFORMATION: Target sequence 1-R

<400> SEQUENCE: 14
gtttccaaag gcaaccgg                                            18

<210> SEQ ID NO 15
<211> LENGTH: 18
<212> TYPE: DNA
<213> ORGANISM: Artificial Sequence
<220> FEATURE:
<223> OTHER INFORMATION: Target sequence 2-F

<400> SEQUENCE: 15
ttgaagccga aatgatga                                            18

<210> SEQ ID NO 16
<211> LENGTH: 18
<212> TYPE: DNA
<213> ORGANISM: Artificial Sequence
<220> FEATURE:
<223> OTHER INFORMATION: Target sequence 2-R

<400> SEQUENCE: 16
gtttccaaag gcaaccgg                                            18

<210> SEQ ID NO 17

```
-continued

<211> LENGTH: 18
<212> TYPE: DNA
<213> ORGANISM: Artificial Sequence
<220> FEATURE:
<223> OTHER INFORMATION: Target sequence 3-F

<400> SEQUENCE: 17
gtcacgctcc gcatcaga                                              18

<210> SEQ ID NO 18
<211> LENGTH: 18
<212> TYPE: DNA
<213> ORGANISM: Artificial Sequence
<220> FEATURE:
<223> OTHER INFORMATION: Target sequence 3-R

<400> SEQUENCE: 18
tgagcgatca agtcgaga                                              18
```

NUCLEOTIDE SEQUENCE AND METHOD FOR CONTROLLING INSECT INFESTATION

CROSS-REFERENCE TO RELATED APPLICATIONS

This application is a § 371 national phase of International Application No. PCT/CN2016/109177, filed on Dec. 9, 2016, which claims priority to Chinese invention patent application No. 2016100004410.2 filed Jan. 4, 2016, which applications are incorporated by reference herein in their entireties.

TECHNICAL FIELD

The present invention relates to a nucleotide sequence and method for controlling insect invasions, particularly to a method for controlling *Lygus* by reducing or shutting off expression of a target sequence in *Lygus* using RNAi technology.

BACKGROUND ART

Field crops are usually the targets of insect attacks. In the last few decades, there has been some substantive progress in developing more effective methods and compositions for insect invasions in crops. Chemical pesticides are relatively effective means for controlling pest invasions. However, the use of chemical pesticides also has many disadvantages. Firstly, chemical pesticides are non-selective, and as people intend to apply chemical pesticides for controlling harmful insects to a variety of crops and other plants, the chemical pesticides also cause damage to non-target organisms, such as earthworms, due to their deficiency in selectivity. Moreover, after applying chemical pesticides for a period of time, the field usually becomes barren. Chemical pesticides will be present in the environment persistently, and will usually be metabolized slowly. Such a slow metabolism results in the presence of chemical pesticide residues in the crops and environment, which will be accumulated in the food chain, particularly in the food chain of higher carnivorous animals. The accumulation of these chemical pesticides results in the induction of diseases in higher species, for example cancers in humans. Therefore, there is a strong demand for an environmentally-friendly method for controlling or eradicating insect invasions in crop production, i.e., a selective, environmentally-friendly method with biodegradability, which can also be used well in a pest resistance management system.

In the last few decades, development of an effective method for controlling plant insect pests has achieved substantive progress. Chemical pesticides are very effective for eradicating plant pests; however, these pesticides also act on non-target insects, and furthermore, chemical pesticides are present in the environment persistently, which not only causes irreversible environmental pollution, but also results in the emergence of pesticide resistant insects. Microbial pesticides, particularly pesticides obtained from the strain of *Bacillus thuringiensis*, abbreviated to Bt, play an important role in agricultural production as a surrogate for chemical pesticides, and have a certain insecticidal activity on insects including *Lepidoptera, Diptera, Coleoptera, Hemiptera*, etc. However, microbial pesticides have a relatively high requirement for the pesticide application environment, and if the environment is not suitable for the growth of these microorganisms, repeated application needs to be performed during production, and in some cases, repeated application cannot even achieve the purpose of controlling pests, thereby greatly increasing the production cost. Some transgenic plants which have enhanced resistance to the pests can be obtained by introducing one or more genes encoding Bt insecticidal proteins into the plants through genetic engineering, for example, genetically engineered maize and cotton plants capable of producing Cry toxins have been widely used in agricultural production in the USA and provide the farmers with an alternative solution of traditional pest control methods. However, the currently developed transgenic crops containing Cry toxins can only be used for preventing and controlling a narrow range of pests, and there are still no products capable of preventing and controlling piercing-sucking pests. Piercing-sucking pests are becoming major pests in developed transgenic crops due to their fast reproduction rates and wide distribution areas.

An antisense method and composition have been reported in the art and are believed to function through synthesis of a single-stranded RNA molecule (theoretically capable of hybridizing with a highly complementary sense strand of RNA molecule in vivo). It is difficult to use antisense technology in many systems for three major reasons. Firstly, an antisense sequence expressed in a transformed cell is not stable. Secondly, the instability of the antisense sequence expressed in the transformed cell accordingly results in difficulty in delivering the sequence to a host, a cell type or a biological system far away from the transgenic cell. Thirdly, with the difficulties encountered in the instability and the delivery of the antisense sequence, another difficulty is also generated for the following purpose: providing a dose capable of effectively regulating the expression level of a target sense nucleotide sequence in a recombinant cell encoding the antisense sequence.

RNA interference or RNAi is a method for downregulating gene expression in a sequence specific manner in a cell or a whole organism environment, in which the purpose of directed interference with the expression of a target gene can be achieved by the specific targeting selection and efficient mRNA repression. Although it is known in the art that the RNAi technology can be used for preventing and controlling pests, a key factor for using such a technique as a measure for controlling insect invasions is selecting the mostly suitable target gene, i.e., a gene, the function of which is lost, thereby resulting in severe disruption of the necessary biological processes and/or death of organisms. Therefore, the present invention achieves the control of insect invasions, particularly the control of insect invasions in a plant, by means of downregulating a specific target gene in a pest.

SUMMARY OF THE INVENTION

The purpose of the present invention is to provide a nucleotide sequence and method for controlling insect invasions, i.e., downregulating the expression of a target sequence using the RNAi technology in a manner of weakening the abilities of an insect to survive, grow, reproduce, colonize in a specific environment and/or invade a host, so as to achieve the control of insect invasions and damages caused thereby.

In order to achieve the above-mentioned purpose, the present invention provides following technical solutions, specifically:

In one aspect, the present invention provides an isolated polynucleotide sequence, comprising:

(a) a polynucleotide sequence as shown in SEQ ID NO: 1, 2 or 3; or (b) a polynucleotide sequence hybridizing with the polynucleotide sequence defined in (a) under stringent conditions; or (c) a polynucleotide sequence having an identity of not less than 80% to the polynucleotide sequence defined in (a); or (d) a polynucleotide sequence of at least 17 consecutive nucleotides of the polynucleotide sequence defined in (a), wherein a double-stranded RNA comprising at least one strand complementary to the polynucleotide sequence, when ingested by an insect pest from *Hemiptera*, inhibits growth of the insect pest from *Hemiptera*; or (e) a complementary sequence of the polynucleotide sequence as defined in (a), (b), (c) or (d).

Preferably, the polynucleotide sequence also comprises a complementary sequence of the polynucleotide sequence, and/or the polynucleotide sequence also comprises a spacer sequence.

More preferably, the polynucleotide sequence is SEQ ID NO: 4, 5 or 6.

In another aspect, the present invention provides an expression cassette, comprising the polynucleotide sequence under regulation of an effectively linked regulatory sequence.

In another aspect, the present invention provides a recombinant vector comprising the polynucleotide sequence or the expression cassette.

In another aspect, the present invention also provides use of the polynucleotide sequence for interfering with expression of a target sequence in an insect pest from *Hemiptera* or inhibiting growth of the insect pest from *Hemiptera*.

In another aspect, the present invention also provides an interfering ribonucleic acid sequence, wherein the interfering ribonucleic acid sequence acts to downregulate expression of at least one target sequence in an insect pest from *Hemiptera* after being ingested by the insect pest, wherein the interfering ribonucleic acid sequence comprises at least one silencing element, wherein the silencing element is a double-stranded RNA region comprising complementary strands being annealed, and one strand of which comprises or consists of a nucleotide sequence at least partially complementary to a target fragment within the target sequence, and the target sequence comprises the polynucleotide sequence.

Preferably, the silencing element comprises or consists of a sequence of at least 19 consecutive nucleotides at least partially complementary to a target fragment within the target sequence.

Furthermore preferably, the interfering ribonucleic acid sequence comprises at least two silencing elements, each of which comprises or consists of a nucleotide sequence at least partially complementary to a target fragment within the target sequence.

Preferably, each of the silencing elements comprises or consists of a different nucleotide sequence complementary to a different target fragment.

More preferably, the different target fragments are derived from the same target sequence or from different target sequences.

Further preferably, the different target sequences are derived from the same insect pest from *Hemiptera* or difficult insect pests from *Hemiptera*.

Most preferably, the insect pest of *Hemiptera* is *Lygus*.

Based on the above-mentioned technical solution, the interfering ribonucleic acid sequence also comprises a spacer sequence.

Particularly, the interfering ribonucleic acid sequence is SEQ ID NO: 4, 5 or 6.

In another aspect, the present invention also provides a composition for controlling invasion of an insect pest from *Hemiptera*, comprising at least one of the interfering ribonucleic acid sequences and at least one suitable carrier, excipient or diluent. Preferably, the composition comprises a host cell expressing or capable of expressing the interfering ribonucleic acid sequence. Particularly, the host cell is a bacterial cell.

Preferably, the composition is a solid, a liquid or a gel. Particularly, the composition is an insecticidal spray.

Optionally, the composition also comprises at least one pesticide, wherein the pesticide is a chemical pesticide, a potato tuber-specific protein, a *Bacillus thuringiensis* insecticidal protein, a *Xenorhabdus ehlersii* insecticidal protein, a *Photorhabdus* insecticidal protein, a *Bacillus laterosporus* insecticidal protein or a *Bacillus sphaericus* insecticidal protein.

In another aspect, the present invention also provides use of the composition for controlling invasion of an insect pest from *Hemiptera* for preventing and/or controlling invasion of an insect pest from *Hemiptera*.

In another aspect, the present invention also provides a method for controlling invasion of an insect pest from *Hemiptera*, comprising contacting the insect pest from *Hemiptera* with an effective amount of at least one of the interfering ribonucleic acid sequence.

In another aspect, the present invention also provides a method for producing a plant capable of controlling an insect pest from *Hemiptera*, comprising introducing the polynucleotide sequence or the expression cassette or the recombinant vector into the plant.

In another aspect, the present invention also provides a method for protecting a plant from damage caused by an insect pest from *Hemiptera*, comprising introducing the polynucleotide sequence or the expression cassette or the recombinant vector into the plant, wherein when ingested by the insect pest from *Hemiptera*, the plant being introduced inhibits growth of the insect pest.

Based on the above-mentioned technical solution, the plant is soybean, wheat, barley, maize, tobacco, rice, rape, cotton or sunflowers. The insect pest from *Hemiptera* is *Lygus*.

In another aspect, the present invention provides a plant capable of controlling an insect pest from *Hemiptera* produced by the method.

In another aspect, the present invention provides a plant cell, plant protoplast, plant tissue culture, plant callus, plant or bacterium capable of controlling an insect pest from *Hemiptera*, wherein the plant cell, plant protoplast, plant tissue culture, plant callus, plant or bacterium comprises the polynucleotide sequence or the expression cassette or the recombinant vector.

Preferably, the plant is soybean, wheat, barley, maize, tobacco, rice, rape, cotton or sunflower, and the plant tissue is an embryo, pollen, ovule, seed, leaf, flower, branch, fruit, kernel, ear, cob, husk, stalk, root, or root tip.

In another aspect, the present invention provides use of the plant or the plant cell, plant protoplast, plant tissue culture, plant callus, plant or bacterium for controlling an insect pest from *Hemiptera*.

The present invention comprises a method for regulating or inhibiting the expression of one or more target sequences in an insect pest from *Hemiptera*, the method comprising: introducing part or all of a stabilized double-stranded RNA (such as dsRNA) or a modified form thereof (for example, a small interfering RNA sequence) into a cell of an invertebrate harmful insect or an extracellular environment thereof. In the insect body, the dsRNA or siRNA enters the cell, inhibits the expression of at least one or more target sequences, and such an inhibition results in the weakening of the abilities of the insect to survive, grow, reproduce and invade a host.

The present invention provides a set of isolated and purified polynucleotide sequences, as shown in SEQ ID NO: 1 to SEQ ID NO: 3. The present invention provides a stabilized double-stranded RNA molecule for inhibiting the expression of a target sequence from these sequences and fragments in a pest from *Hemiptera*. The stabilized double-stranded RNA comprises at least two coding sequences, which are arranged in the sense and antisense directions relative to at least one promoter, wherein the nucleotide sequences comprising a sense strand and an antisense strand are connected or linked via a spacer sequence of at least about 5-1000 nucleotides, wherein the sense strand and antisense strand can be of different lengths, and wherein at least one of the two coding sequences has at least 80%, at least 90%, at least 95%, at least 98%, or 100% sequence identity to any one or more of the nucleotide sequences shown in SEQ ID NO: 1 to SEQ ID NO: 3.

When being expressed as a dsRNA and administrated to a pest, the fragment can be defined as one resulting in death, and inhibited, hindered or halted feeding activity of the pest. The fragment can, for example, comprise at least about 19, 21, 23, 25, 40, 60, 80, 100, 125 or more consecutive nucleotides or about 19 to about 100 nucleotides, or more, of any one or more sequences of SEQ ID NO: 1 to SEQ ID NO: 3 or the complementary sequences thereof. Particularly useful is a dsRNA sequence comprising about 19,300 nucleotides homologous to the target sequence of pest. The present invention also provides an RNA expressed by any of the polynucleotide sequences, including dsRNA. A sequence selected for expressing a gene inhibitor and for expressing an RNA inhibiting a single gene or gene family in one or more target pests can be constructed using a single sequence from one or more target pests, or the DNA sequence can be constructed as a chimera from a variety of DNA sequences.

The plant in the present invention can include any propagation or reproduction material of a plant, and can also include a plant cell, a plant protoplast, a plant tissue culture, a plant callus and an intact plant cell in a plant or portions thereof, with these plant portions being, for example, embryos, pollen, ovules, seeds, leaves, flowers, branches, fruits, kernels, ears, cobs, husks, stalks, roots, or root tips.

The *Lygus* in the present invention belongs to the Miridae family of *Hemiptera*, and is a class of pests of particular relevance in agricultural production. Currently, common species in our country are *Apolygus lucorum* (Meyer-Dur), *Adelphocoris suturalis* (Jakovlev), *Adelphocoris fasciaticollis* (Reuter), *Adelphocoris lineolatus* (Goeze), *Lygus pratensis* (Linnaeus) and the like. *Apolygus lucorum* is the most harmful, and adult insects cause damage by piercing and sucking plant juices with stingers, and favor ingestion of flowers, buds, fruits, and other reproductive organs of a plant.

The expression "controlling an insect" or "controlling a pest" or "controlling an insect pest" in the present invention means any effect on an insect which can result in limitation of the damage caused by the insect, including, but not limited to, killing the insect, inhibiting development of the insect, changing fertility or growth of the insect in such a manner that the insect can only cause less damage to the plant, reducing the quantity of progenies generated by the insect, producing less normal insects, producing insects which will be more easily attacked by predators or preventing the insects from eating the plants.

The expression "target sequence" in the present invention means any sequence intended to be downregulated in an insect. Insect infestations are controlled by downregulating the target sequence, for example by disrupting necessary biological processes in the insects. Therefore, preferred target sequences include, but are not limited to, genes playing essential roles in regulating feeding activity, survival, growth, development, reproduction, invasion and infection. When the expression of the target sequence is downregulated or inhibited, at least 20% of the insects are killed; or the growth of at least 20% of the insects is prevented/slowed/hindered/delayed/blocked, the reproduction of at least 20% of the insects is prevented, and the change in at least 20% of the insects through their life cycle is prevented; or the damage caused by the insects and/or the abilities of the insects to infect or infest the environment, surface and/or plants or crop species is decreased; or at least 20% of the insects are stopped feeding from natural food sources thereof (such as a plant and a plant product). These target sequences can be expressed in all or a portion of insect cells. Additionally, these target sequences can be only expressed in a specific stage in a life cycle of the insects, for example in the adult stage, larval phase or egg stage.

In the present invention, the term "pest" is preferably an insect causing plant invasion/infestation/infections, and belongs to *Hemiptera*, preferably *Lygus*. The terms "infestation", "infection" and/or "invasion" can be generally used interchangeably throughout the document.

The term "RNA interference (RNAi)" in the present invention means some RNAs that can efficiently and specifically block the expression of a specific gene in vivo, promote the degradation of mRNA, and induce a cell to exhibit a specific gene deletion phenotype; this technology is also referred to as RNA intervention or interference. RNA interference is a highly specific gene silencing mechanism at the mRNA level.

The term "nucleic acid" in the present invention means a single-stranded or double-stranded polymer of deoxyribonucleic acid or ribonucleic acid bases read from the 5' terminus to 3' terminus. Optionally, the term "nucleic acid" can also comprise non-naturally occurring or changed bases which allow correct reading by a polymerase and will not reduce the expression of a polypeptide encoded by the nucleic acid. The term "nucleotide sequence" means a sense and an antisense strand of a nucleic acid present as individual single strands or present in a dimer. The term "ribonucleic acid" (RNA) includes RNAi (RNA interference), dsRNA (double-stranded RNA), siRNA (small interfering RNA), mRNA (messenger RNA), miRNA (microRNA), tRNA (transfer RNA charged with or without corresponding acylated amino acids) and cDNA and genomic DNA, as well as DNA-RNA hybrids. The term "nucleic acid fragment", "nucleic acid sequence fragment" or the more commonly-known term "fragment" will be understood by a person skilled in the art to include a genomic sequence, a ribosomal RNA sequence, a transfer RNA sequence, a messenger RNA sequence, an operon sequence and a smaller engineered nucleotide sequence, wherein these sequences express or can be engineered to express a protein, a polypeptide or a peptide.

The term "interfering ribonucleic acid" in the present invention covers any type of RNA molecule capable of downregulating or "silencing" the expression of a target sequence, including, but not limited to, sense RNA, antisense RNA, short interfering RNA (siRNA), microRNA (miRNA), double-stranded RNA (dsRNA), hairpin RNA (hpRNA), and the like. Methods for measuring functional interfering RNA molecules are well known in the art and have been disclosed.

The interfering ribonucleic acid in the present invention achieves specific downregulation of the expression of a target sequence by binding to a target fragment within a target sequence. The reason for the occurrence of the binding is the base pairing between the complementary regions of the interfering RNA and the target fragment. The term "silencing element" refers to a part or region of an interfering ribonucleic acid comprising or consisting of a nucleotide sequence complementary to or at least partially complementary to a target fragment within a target sequence, wherein the part or region acts as an active part of the interfering ribonucleic acid so as to direct the downregulation of the expression of the target sequence. The silencing element comprises a sequence having at least 17 consecutive nucleotides, preferably at least 18 or 19 consecutive nucleotides, more preferably at least 21 consecutive nucleotides, and even more preferably at least 22, 23, 24 or 25 consecutive nucleotides complementary to a target fragment within a target sequence; or an interfering ribonucleic acid consisting thereof.

The term "expression of a target sequence" in the present invention refers to the transcription and accumulation of RNA transcripts encoded by a target sequence and/or translation of mRNA into a protein. The term "downregulation" refers to any of the methods known in the art by which an interfering ribonucleic acid reduces the level of primary RNA transcript, mRNA or protein produced from a target sequence. The downregulation refers to a situation whereby the level of RNA or proteins produced from a gene is reduced by at least 10%, preferably at least 33%, more preferably at least 50%, and even more preferably at least 80%. Specifically, downregulation refers to the reduction of the level of RNA or proteins produced from a gene in an insect cell by at least 80%, preferably at least 90%, more preferably at least 95%, and most preferably at least 99%, as compared with a suitably controlled insect (for example, an insect which has not been exposed to the interfering ribonucleic acid or has been exposed to a control interfering ribonucleic acid). Methods for detecting the reduction of RNA or protein levels are well known in the art, and include RNA solution hybridization, Northern hybridization, reverse transcription (for example quantitative RT-PCR analysis), microarray analysis, antibody binding, enzyme-linked immunosorbent assay (ELISA) and Western blotting. Meanwhile, downregulation can also mean that, as compared with the suitable insect control, the level of RNA or proteins is reduced to a level sufficient to result in the insect phenotype generating a detectable change, for example cell death, growth cessation, and the like. Therefore, downregulation can be measured by phenotype analysis of the insect using conventional techniques in the art.

The expression "inhibition of expression of a target sequence" in the present invention refers to the reduction or absence (below a detectable threshold) of the level of the proteins and/or mRNA product of the target sequence. Specificity refers to an ability to inhibit a target sequence and produce no effect on other genes in a cell, and brings about no effect on any gene in a cell generating dsRNA molecules.

The "sense" RNA in the present invention refers to an RNA transcript corresponding to a sequence or fragment present in the form of mRNA which can be translated into a protein by a plant cell. The "antisense" RNA in the present invention refers to RNA complementary to all or part of mRNA produced normally in a plant. The complementation of an antisense RNA can be directed at any part of a transcript of a specific gene, i.e. a 5' non-coding sequence, 3' non-coding sequence, intron or coding sequence. The term "RNA transcript" in the present invention refers to a product obtained by transcription on the DNA sequence catalyzed by an RNA polymerase. When the RNA transcript is a completely complementary copy of a DNA sequence, the RNA transcript is referred to as a primary transcript, or is an RNA obtained by post-transcriptional processing of the primary transcript, which is referred to as a mature RNA.

The interfering ribonucleic acid in the present invention downregulates the expression of a gene by RNA interference or RNAi. RNAi is a typical method for sequence specific gene regulation mediated by a double-stranded RNA molecule (such as short interfering RNA (siRNA)). siRNA comprises a sense RNA strand being annealed with an antisense RNA strand by complementary base pairing. The sense strand or "leading strand" in a siRNA molecule comprises a nucleotide sequence complementary to a nucleotide sequence located within an RNA transcript of a target sequence. Therefore, the sense strand of siRNA can be annealed with the RNA transcript by Waston-Crick-type base pairing, and targets the RNA so that the RNA is degraded in a cellular complex referred to as RNAi induced silencing complex (or RISC). In the case of a preferred interfering ribonucleic acid in the present invention, the silencing element can be a double-stranded region comprising complementary strands being annealed, at least one strand of which comprises a nucleotide sequence complementary or at least partially complementary to a target fragment sequence within a target sequence; or comprises an interfering ribonucleic acid consisting thereof. The double-stranded region has a length of at least about 19 to about 25 base pairs, or a length of about 25 to about 100 base pairs, or even a length of about 3000 base pairs.

The dsRNA molecule in the present invention can serve as a precursor for active siRNA molecules which direct RNA transcripts to the RISC complex for subsequent degradation. A dsRNA molecule present in an organism or the cellular surroundings thereof can be ingested by the organism and processed by an enzyme known as DICER to obtain a siRNA molecule. Optionally, a dsRNA molecule can be produced in vivo, i.e., one or more polynucleotides encoding the dsRNA present in a cell (for example, a bacterial cell or a plant cell) are transcribed, and processed by DICER in a host cell or preferably in an insect cell after ingesting a longer precursor dsRNA. The dsRNA can be formed by two separate (sense and antisense) RNA strands being annealed by complementary base pairing. Alternatively, dsRNA can be a single strand, which can refold itself to form a hairpin RNA or a stem-loop structure. In the case of one single RNA, the double-stranded region or "stem" is formed of two regions or segments of the RNA, wherein these regions or segments are substantially inverted repeat sequences for each other, and have sufficient complementarity to allow the formation of a double-stranded region. One or more functional double-stranded silencing elements can be present in this "stem region" of the molecule. Inverted repeat regions are typically spaced via a region or segment referred to as a "loop" region in an RNA. This region can comprise any nucleotide sequence which confers sufficient flexibility to allow self-pairing between flanking complementary regions of RNA, and in general, the loop region is substantively single stranded and serves as a spacer sequence between inverted repeat sequences.

The interfering ribonucleic acid in the present invention comprises at least one double-stranded region, typically a silencing element of the interfering ribonucleic acid, which comprises a sense RNA strand being annealed with an antisense RNA strand by complementary base pairing, wherein the sense strand of the dsRNA molecule comprises a nucleotide sequence complementary to a nucleotide sequence located within the RNA transcript of a target sequence. The silencing element or at least one strand thereof (when the silencing element is double stranded) can be completely or partially complementary to a target fragment of a target sequence. The term "completely complementary" means that all the bases of the nucleotide sequence of a silencing element are complementary to or "match" the bases of a target fragment. The term "at least partially complementary" refers to less than 100% of matching degree being present between the bases of a silencing element and the bases of a target fragment. A person skilled in the art would understand that in order to mediate the downregulation of the expression of a target sequence, the silencing element only needs to be at least partially complementary to the target fragment. It is known in the art that an RNA sequence having an insertion, deletion and mismatch with respect to the target sequence can still be effective in terms of RNAi. Preferably, the silencing element and the target fragment of the target sequence share at least 80% or 85% sequence identity, preferably at least 90% or 95% sequence identity, or more preferably at least 97% or 98% sequence identity, and still more preferably at least 99% sequence identity. Optionally, over each length of 24 partially complementary nucleotides, as compared with the target fragment, the silencing element can comprise 1, 2 or 3 mismatches. It is well known to a person skilled in the art that the complementarity degree shared between the silencing element and the target fragment varies with the target sequence to be downregulated or the insect species to be controlled by gene expression.

The target fragment in the present invention can be selected from any suitable region or nucleotide sequence of a target sequence or an RNA transcript thereof. For example, the target fragment can be located within the 5' UTR or 3' UTR of the target sequence or RNA transcript, or within an extron or intron region of the gene.

The interfering ribonucleic acid in the present invention can comprise one or more silencing elements, wherein each silencing element comprises or consists of a nucleotide sequence at least partially complementary to a target fragment within a target sequence, and functions to downregulate the expression of the target sequence after being ingested by an insect. The term "a plurality of" or "more" means at least two, at least three, at least four, and so on until at least 10, 15, 20 or at least 30. The interfering ribonucleic acid comprises a plurality of copies of a single silencing element, i.e., repeats of the silencing element binding to a specific target fragment within a specific target sequence. The silencing element within the interfering ribonucleic acid can also comprise or consist of different nucleotide sequences complementary to different target fragments. It shall be apparent that a combination of a plurality of copies of the same silencing element with a silencing element binding to a different target fragment also falls within the scope of the present invention.

In the present invention, in order to achieve the downregulation of a specific target sequence in an insect from Hemiptera, different target fragments can be derived from a single target sequence in an insect. In this case, silencing elements in an interfering ribonucleic acid can be combined according to the original order of target fragments present in a target sequence, or as compared with the order of the target fragments in the target sequence, the silencing elements can be disorganized and randomly combined in any rank order in an environment of the interfering ribonucleic acid.

Optionally, different target fragments represent a single target sequence respectively, but are derived from different insect species.

Optionally, different target fragments can be derived from different target sequences. If an interfering ribonucleic acid is used for preventing and/or controlling pest invasions, then it is preferred that different target sequences are selected from the group consisting of genes regulating necessary biological functions in an insect, wherein these biological functions include, but are not limited to, survival, growth, development, reproduction and pathogenicity. The target sequences can regulate the same or different biological pathways or processes.

In the present invention, different genes targeted by different silencing elements can be derived from the same insect. This method can be used for achieving an enhanced attack against a single insect. Particularly, different target sequences can be differentially expressed in different stages of life cycle of the insect, for example the mature adult stage, immature larval stage and egg stage. Therefore, the interfering ribonucleic acid in the present invention can be used for preventing and/or controlling insect invasions in one or more than one stages of the life cycle of the insect. Alternatively, different genes targeted by different silencing elements are derived from different insects; therefore, the interfering ribonucleic acid in the present invention can also be used for simultaneously preventing and/or controlling invasions of one or more types of insects.

The silencing element in the present invention can be a consecutive region of an interfering ribonucleic acid or can be spaced apart via a linker sequence. The linker sequence can comprise a short random nucleotide sequence not complementary to any target fragment or target sequence. The linker sequence can be a conditional self-cleavage RNA sequence, preferably a pH sensitive linker or a hydrophobic sensitive linker. The linker can also comprise a nucleotide sequence equivalent to an intron sequence. The length of the linker sequence can be in a range of 1 base pair to about 10000 base pairs, provided that the linker will not weaken the ability of the interfering ribonucleic acid to downregulate the gene expression.

In addition to one or more silencing elements and any linker sequence, the interfering ribonucleic acid in the present invention can also comprise at least one additional polynucleotide sequence. The additional polynucleotide sequence is selected from: (1) a sequence capable of protecting the interfering ribonucleic acid from RNA processing; (2) a sequence affecting the stability of the interfering ribonucleic acid; (3) a sequence which allows binding of a protein to facilitate the ingestion of the interfering ribonucleic acid by an insect cell; (4) a sequence facilitating the large-scale production of the interfering ribonucleic acid; (5) an aptamer sequence capable of binding to an receptor or binding to a molecule on surface of an insect cell so as to facilitate the ingestion; or (6) a sequence catalyzing the processing of the interfering ribonucleic acid in an insect cell and thereby enhancing the efficacy of the interfering ribonucleic acid.

The length of the interfering ribonucleic acid in the present invention needs to be sufficient to be ingested by an insect cell and downregulate a target sequence in the insect. The upper limit of the length can depend on: (1) the requirement for ingestion of the interfering ribonucleic acid by an insect cell, and (2) the requirement of the interfering ribonucleic acid in the insect cell being processed to mediate gene silence through an RNAi approach, and the length can also be specified by a method of production and a formulation for delivering the interfering ribonucleic acid to the cell. Preferably, the length of the interfering ribonucleic acid in the present invention will be between 19 and 10000 nucleotides, preferably between 50 and 5000 nucleotides or between 100 and 2500 nucleotides, more preferably having a length between 80 and 2000 nucleotides.

The interfering ribonucleic acid in the present invention can comprise DNA bases, unnatural bases or an unnatural backbone connection or modifications of a sugar-phosphate backbone, for example, for enhancing the stability during storage or enhancing the resistance to nuclease degradation. Additionally, the interfering ribonucleic acid can be produced chemically or enzymatically through a manual or automatic reaction by a person skilled in the art. Optionally, the interfering ribonucleic acid can be transcribed from a polynucleotide encoding thereof. Therefore, the present invention provides an isolated polynucleotide for encoding any one of the interfering ribonucleic acid.

The polynucleotide in the present invention can be inserted into a DNA construct or a vector known in the art by a conventional molecular cloning technique. The DNA construct can be a recombinant DNA vector, for example, a bacterial, viral or yeast vector. The DNA construct is an expression construct, in which the polynucleotide is operably linked to at least one regulatory sequence capable of driving the expression of the polynucleotide sequence. The term "regulatory sequence" refers to any nucleotide sequence capable of affecting the expression of an operably linked polynucleotide, including, but not limited to, a promoter, an enhancer, and other naturally generated or synthesized transcriptional activation elements. The regulatory sequence can be located at the 5' or 3' terminus of the polynucleotide sequence. The term "operably linked" refers to a functional connection between a regulatory sequence and a polynucleotide sequence, with the connection resulting in the regulatory sequence driving the expression of the polynucleotide. Operably linked elements can be consecutive or inconsecutive.

The regulatory sequence in the present invention can be a promoter. Preferably, the promoter is a plant expressible promoter. The "plant expressible promoter" refers to a promoter that ensures the expression of the polynucleotide linked thereto in a plant cell. The plant expressible promoter can be a constitutive promoter. Examples of promoters directing the constitutive expression in plants include, but are not limited to, a 35S promoter derived from cauliflower mosaic virus, maize ubi promoters, rice GOS2 gene promoters, and the like. Alternatively, the plant expressible promoter can be a tissue specific promoter, i.e. the promoter directs the expression of an coding sequence in several tissues, such as green tissues, at a level higher than in other tissues of the plant (which can be measured through conventional RNA trials), such as a PEP carboxylase promoter. Alternatively, the plant expressible promoter can be a wound-inducible promoter. The wound-inducible promoter or a promoter directing the expression mode induced by the wound means that when a plant suffers from a wound caused by a mechanical factor or the gnawing of insects, the expression of the polynucleotide under the regulation of the promoter is significantly improved than when under normal growth conditions. Examples of the wound-inducible promoters include, but are not limited to, promoters of potato and tomato protease inhibitor genes (pinI and pinII) and maize protease inhibitor genes (MPI).

Optionally, one or more transcription termination sequences can be incorporated into the expression construct in the present invention. The term "transcription termination sequence" covers a control sequence at the terminus of a transcription unit, and sends signals regarding the transcription termination, 3' processing and polyadenylation of a primary transcript. The additional regulatory element includes, but is not limited to, a transcription or translation enhancer which can be incorporated into an expressed construct, for example, a double enhancing CaMV35S promoter.

The method for producing any interfering ribonucleic acid in the present invention comprises the steps of: (1) contacting the polynucleotide encoding the interfering ribonucleic acid or a DNA construct comprising the polynucleotide with a component free of cells; and (2) introducing the polynucleotide encoding the interfering ribonucleic acid or the DNA construct comprising the polynucleotide (for example, through transformation, transfection or injection) into a cell.

In the present invention, a host cell comprising any interfering ribonucleic acid of the present invention, any polynucleotide of the present invention or a DNA construct comprising these polynucleotides can be a prokaryotic cell, including, but not limited to, Gram-positive and Gram-negative bacterial cells; or a eukaryotic cell, including, but are limited to, a yeast cell or a plant cell. Preferably, the host cell is a bacterial cell or a plant cell. The polynucleotide or DNA construct in the present invention can be present or maintained as an extrachromosomal element in the host cell, or can be stably incorporated into the genome of the host cell.

In the present invention, in the case of an interfering ribonucleic acid being expressed in a host cell and/or used for preventing and/or controlling insect infestations in a host organism, it is preferred that the interfering ribonucleic acid does not exhibit a significant "off-target" effect, i.e., the interfering ribonucleic acid does not affect the expression of a non-target sequence in the host. Preferably, the silencing gene does not exhibit significant complementarity to a nucleotide sequence apart from a given target fragment of the target sequence. The silencing element shows less than 30%, more preferably less than 20%, more preferably less than 10%, and even more preferably less than 5% sequence identity to any gene of the host cell or organism. If the genomic sequence data of the host organism is available, then the identity to the silencing element can be cross-checked using standard bioinformatics tools. Within a region having 17 consecutive nucleotides, more preferably within a region having 18 or 19 consecutive nucleotides, and most preferably within a region having 19 or 20 or 21 consecutive nucleotides, the silencing element and the gene from the host cell or organism do not have sequence identity.

The composition in the present invention for preventing and/or controlling insect infestations comprises at least one interfering ribonucleic acid and optionally at least one suitable carrier, excipient or diluent, wherein the interfering ribonucleic acid functions to downregulate the expression of a target sequence in an insect after being ingested by the insect. The interfering ribonucleic acid comprises or consists of at least one silencing element, and the silencing element is a double-stranded RNA region containing complementary strands being annealed, one strand of which (sense strand) comprises a nucleotide sequence at least partially complementary to a target fragment within a target sequence. The target sequence includes, but is not limited to, genes regulating the survival, growth, development, reproduction and pathogenicity of an insect. Optionally, the composition comprises at least one host cell, and the host cell comprises at least one interfering ribonucleic acid or a DNA construct encoding the interfering ribonucleic acid, and optionally at least one suitable carrier, excipient or diluent, wherein the interfering ribonucleic acid functions to downregulate the expression of a target sequence in an insect after the host cell is ingested by the insect.

The composition in the present invention can be presented as any suitable physical form to be applied to an insect. For example, the composition can be in the form of a solid (powder, pellet or bait), a liquid (including an insecticidal spray) or a gel. The composition can be a coating, paste or powder, which can be applied to a substrate so as to protect the substrate from the insect infestation. The composition can be used for protecting any substrate or material sensitive to the insect invasions or damage caused by the insect.

The properties of the excipient and the physical form of the composition can vary due to the properties of the substrate which is desired to be treated. For example, the composition can be a liquid which is brushed or sprayed onto a material or substrate to be treated or printed onto a material or substrate to be treated; or a coating or powder which is applied to a material or substrate to be treated.

In the present invention, the composition can be in the form of bait. The bait is used to induce an insect to be contacted with the composition. After being in contact with the insect, the composition is subsequently internalized by the insect through, for example, ingestion and mediates RNAi, thereby killing the insect. The bait can comprise a type of food, such as a type of protein-based food, for example fish meal. Boric acid can also be used as bait. The bait can depend upon the species to be targeted. An attractant can also be used, which, for example, can be a pheromone such as a male or female pheromone. The attractant can act to induce the contact between the insect and the composition, and can be targeted at a specific insect or can attract insects over the whole range, increasing the contact chance of the induced insects and the composition of the present invention, thereby achieving the purpose of killing a mass of insects. The bait can be in any suitable form, such as the form of a solid, a paste, a pellet or a powder.

The bait can also be taken to the insect community by the insects. The bait can then serve as a food source of other members in the community, thereby providing an effective control for a mass of insects and potentially the whole insect community. The bait can also be provided in a suitable "shell" or "trapper".

Additionally, the composition in contact with the insects can be held on the surface of the insects. Upon cleaning, whether cleaning a single insect on its own or cleaning each other, the composition can be ingested and can thus mediate the effect thereof in the insects. For this, the composition needs to be sufficiently stable, so that even when exposed to external environment conditions for a period of time (for example, several days), the interfering ribonucleic acid still remains intact and can mediate RNAi.

The composition in the present invention can be provided in the form of a spray. Therefore, a human user can directly spray the insects with the composition. The composition is then internalized by an insect, and can mediate RNA interference in the insect body, thereby controlling the insect. The spray is preferably a pressurized/atomized spray or a pump spray. These particles can have a suitable size so that they can be adhered to the insect, for example, adhered to the exoskeleton where the particles can be absorbed.

In the present invention, the carrier of the composition is an electrostatic powder or particle which can be adhered to an insect. Optionally, the carrier of the composition can comprise magnetic particles which can be adhered to the surface of the insect. Optionally, the carrier of the composition comprises metal particles which are initially unmagnetized, but can become magnetically polarized upon entering an electric field provided by the insect body. Preferably, the composition is incorporated into a carrier which increases the ingestion of an interfering RNA by the insect. Such a carrier can be a lipid-based carrier, preferably including one or more of the following: an oil-in-water type emulsion, a micelle, cholesterol, lipopolyamine and lipidosome. Other agents improving the ingestion of the construct in the present invention are well known to a person skilled in the art, and include polycations, dextran and cationic lipids such as CS096 and CS102. Optionally, the carrier of the composition is a coagulant for nucleic acid, and preferred coagulant comprises spermidine or protamine sulfate, or derivatives thereof.

In the case that the composition in the present invention is suitable for preventing and/or controlling insect invasions in a plant, the composition can comprise an agriculturally suitable carrier. Such a carrier can be any material which can be tolerated by a plant to be treated, and the material would not cause inappropriate damage to the environment or other organisms therein, and allows the effect of the interfering ribonucleic acid on the insect to be maintained. In particular, the composition of the present invention can be formulated in accordance with the conventional agricultural practice used in the industry of biological pesticides, so as to be delivered to a plant. The composition can comprise additional components capable of performing other functions, wherein these functions include, but are not limited to, (1) enhancing or improving the ingestion of the interfering ribonucleic acid by an insect cell, and (2) stabilizing the active components of the composition. Such additional components contained in the composition comprising the interfering ribonucleic acid can be a yeast tRNA or yeast total RNA.

The composition can be formulated for direct application or formulated as a concentrated form of a primary composition which needs to be diluted prior to use. Optionally, the composition can be provided in the form of a kit comprising the interfering ribonucleic acid or a host cell comprising/expressing the interfering ribonucleic acid in a container, and a suitable diluent or carrier for the RNA or host cell in a separate container. In the application of the present invention, the composition can be applied to a plant or any part thereof in any development stage of the plant, for example, during the culture of the plant in a field, the composition is applied to the part of the plant which is above the ground; or when the plant seeds are stored or after the plant seeds are sown in the soil, the composition is applied to the plant seeds. In general, it is important to achieve a good control over an insect in an early growth stage of the plant, since this stage is a period when the plant is possibly suffering from most serious insect damage.

In the present invention, the composition can be applied to the environment of insects through different techniques which include, but are not limited to, spraying, atomizing, dusting, scattering, pouring, seed coating, seed treatment, introduction into the soil and introduction into irrigation water. When a plant which is sensitive to insect infestations is treated, the composition can be delivered to the plant or a part thereof before the occurrence of the insect (for a preventative purpose) or after the emergence of signs of an insect invasion (for a control purpose).

The composition of the present invention can be formulated as comprising at least one additional active agent. Therefore, the composition can be provided in the form of a "kit of parts", and the kit comprises a composition comprising an interfering ribonucleic acid in a container, and one or more suitable active components, such as chemical or biological pesticides, in a separate container. Optionally, the composition can be provided in the form of a mixture which is stable and the components of which can be used in combination with each other.

Suitable active components which can be used in a complementary manner with the interfering ribonucleic acid of the present invention include, but are not limited to, the following items: dursban, allethrin, resmethrin, tetrabromoethyl, dimethanol-cyclopropanecarboxylic acid (generally being comprised in a liquid composition); and hydramethylnon, avermectin, dursban, sulfluramid, hydroprene, fipronil (a GABA receptor), carbamic acid isopropyl phenyl methyl ester, indoxacarb, noviflumuron (a chitin synthesis inhibitor), imiprothrin, abamectin (a glutamate gated chloride ion channel), and imidacloprid (an acetylcholine receptor) (generally being comprised in a bait composition). Preferably, taking the health and environment into account, it is known that the active component is an insecticide such as hydramethylnon and avermectin.

The composition in the present invention can be formulated as comprising at least one additional agronomical reagent, such as a herbicide or an additional pesticide. The term "additional pesticide" or "a second pesticide" refers to a pesticide apart from the first or initial interfering RNA molecule of the composition. Optionally, the composition of the present invention can be delivered in combination with at least one additional agronomical reagent (for example a herbicide or a second pesticide). The composition can be provided in combination with a herbicide which is selected from any herbicide known in the art, for example, glyphosate, imidazolinone, sulfonylurea and bromoxynil. The composition can also be provided in combination with at least one additional pesticide which can be selected from any pesticide known in the art and/or can comprise an interfering ribonucleic acid which functions to downregulate the expression of a target sequence in an insect after being ingested by the insect. The target pest is an insect and the interfering ribonucleic acid is selected from any one of the interfering ribonucleic acids in the present invention. The additional pesticide comprises an interfering ribonucleic acid which functions to downregulate the expression of a known gene in any target pest. The initial interfering ribonucleic acid and the second or additional pesticide in the composition can be targeted at the same or different insects. For example, the initial interfering ribonucleic acid and the second pesticide can be targeted at different insects or can be targeted at insects of different families or classes, for example fungi or nematodes or insects. A person skilled in the art should be clear on how to detect a synergistic effect of the combination of the interfering ribonucleic acid and other agronomical reagents. Preferably, the composition comprises a first interfering ribonucleic acid and one or more additional pesticides, each of which has a toxicity for the same insect, wherein the one or more additional pesticides are selected from a potato tuber-specific protein, a *Bacillus thuringiensis* insecticidal protein, a *Xenorhabdus ehlersii* insecticidal protein, a *Photorhabdus* insecticidal protein, a *Bacillus laterosporus* insecticidal protein, a *Bacillus sphaericus* insecticidal protein and lignin. Different components can be delivered simultaneously or successively to a region or organism to be treated.

The method for preventing and/or controlling insect invasions in the present invention comprises contacting an insect with an effective amount of at least one interfering ribonucleic acid, wherein the interfering ribonucleic acid functions to downregulate the expression of a necessary target sequence of insect after being ingested by the insect. The necessary target sequence can be any gene of the insect involved in the regulating of the initiation or maintenance of necessary biological processes required for infestation in the insect, and the biological processes include, but are not limited to, survival, growth, development, reproduction and pathogenicity.

The method for preventing and/or controlling insect invasions in the crop plant field in the present invention comprises expressing an effective amount of the interfering ribonucleic acid in the plant, and in the case that the method is used for controlling insect invasions, the term "effective amount" refers to an amount or concentration of the interfering ribonucleic acid required for producing a phenotypic effect on the insect, so that the number of the insects infesting a host organism is reduced and/or the amount of damage caused by the insect is decreased. The phenotypic effect can be insect death, and the use of the interfering RNA achieves an insect death rate of at least 20%, 30%, 40%, preferably at least 50%, 60%, 70%, and more preferably at least 80% or 90% as compared with a control insect. The phenotypic effect can also include, but is not limited to, the prevention of insect growth, arrest of feeding activity and reduction of egg laying. Therefore, as compared with the control insect, the total number of the insects invading the host organism can be reduced by at least 20%, 30%, 40%, preferably by at least 50%, 60%, 70%, and more preferably by at least 80% or 90%. Optionally, as compared with the control insect, the damage caused by the insect can be reduced by at least 20%, 30%, 40%, preferably by at least 50%, 60%, 70%, and more preferably by at least 80% or 90%. Therefore, the present invention can be used to achieve at least 20%, 30%, 40%, preferably at least 50%, 60%, 70%, and more preferably at least 80% or 90% control of the insect.

The method and composition in the present invention can be used to restrict or eliminate the invasion of a *Hemiptera* pest, preferably *Lygus*, in the environment or on the surface where any pest host, pest symbiont or pest may be present, by providing one or more compositions comprising the dsRNA molecules in the present invention in the food of the pest. The method is especially beneficial for preventing the insect from attacking a plant, and the pest is defined as having a pH of about 4.5 to about 9.5, about 5 to about 9, about 6 to about 7 or about pH 7.0 in the digestive system.

The nucleotide sequence of the present invention can comprise inverted repeats spaced apart by a "spacer sequence". The spacer sequence can be a region comprising any of the following nucleotide sequences, if desired, which can promote the formation of a secondary structure between each segment of repeats. The spacer sequence is a part for a sense or antisense coding sequence of mRNA. Alternatively, the spacer sequence can comprise any combination of nucleotides or homologues thereof which can be covalently linked to a nucleic acid molecule. The spacer sequence can comprise a nucleotide sequence with a length of at least about 10-100 nucleotides, or a length of at least about 100-200 nucleotides, or a length of at least about 200-400 nucleotides, or a length of at least about 400-500 nucleotides.

In the present invention, the "introduction" of the interfering ribonucleic acid into a plant means introduction that can be performed by a direct transformation method, for example, *Agrobacterium*-mediated transformation for a plant tissue, microparticle bombardment, electroporation, etc.; or introduction that can be performed by hybridizing a plant having a heterogenous nucleotide sequence with another plant, so that the progenies have the nucleotide sequence incorporated into their genomes. Such breeding technologies are well known to a person skilled in the art.

The present invention provides a nucleotide sequence and method for controlling insect invasions, having the following advantages:

1. The present invention discloses, for the first time, three target sequences for controlling an insect pest from *Hemiptera, Lygus*, and furthermore, verifies that a nucleic acid inhibitor obtained based on these target sequences is able to be directly used for controlling invasions of insect pests from *Hemiptera*.

2. High specificity. The control in the present invention for a target fragment of an insect pest *Hemiptera, Lygus*, does not affect the expression of a non-target sequence in the host.

3. Avoidance of development of resistance. The present invention provides three target sequences for controlling an insect pest from *Hemiptera, Lygus*, and aperiodic replacement of the target sequences or mixing of the target sequences can prevent the *Lygus* developing resistance.

4. The RNAi technology used in the present invention is efficient and specific, and the dsRNA obtained can be directly used in field for controlling the invasion of insect pests from *Hemiptera*, which is convenient, inexpensive in cost, and good in environment compatibility.

The technical solution of the present invention is further described in details through drawings and examples below.

DESCRIPTION OF THE DRAWINGS

FIG. 1 is a schematic diagram of recombinant expression vector DBN100462 used as the nucleotide sequence and a method for controlling insect invasions in the present invention.

PARTICULAR EMBODIMENTS

The technical solution of the nucleotide sequence and method for controlling insect invasions in the present invention is further described through the particular examples below.

Example 1. Determination of Target Sequences of *Lygus*

1. Total RNA Extraction of *Lygus*

Third instar larvae of *Lygus* were taken as materials, and RNA was extracted using the conventional Trizol method, purified through a conventional method, and treated with a DNase, to thereby obtain a total RNA sample at a concentration of ≥300 ng/μl, a total amount of ≥6 μg, and $OD_{260/280}$ of 1.8-2.2.

2. Separation of mRNA and Synthesis of cDNA mRNA with polyA was separated using magnetic beads with oligo-dTs, and the first strand of cDNA was then synthesized using a random hexamer and a Superscript II reverse transcriptase kit of Invitrogen.

3. Screening Out of Three Target Sequences

Three target sequences of *Lygus* from various metabolic pathways were screened out, with the particular information as follows:

| Target sequence | Sequence number |
|---|---|
| Target sequence 1 | SEQ ID NO: 1 |
| Target sequence 2 | SEQ ID NO: 2 |
| Target sequence 3 | SEQ ID NO: 3 |

Example 2. Construction of Plant Expression Vectors

An expression vector was formed by linking a cauliflower mosaic virus 35S promoter-a sense strand of a target sequence-spacer sequence-antisense strand of a target sequence, with a marker gene Hpt for hygromycin selection.

A sense primer had restriction enzyme sites of EcoR I and Hind III at two ends respectively, an antisense primer had restriction enzyme sites of Xho I and Sac I at two ends respectively, and a primer for the spacer sequence had restriction enzyme sites of Hind III and Sac I respectively.

A recombinant cloning vector containing the sense strand was double digested with EcoR I and Hind III, and a sense strand fragment was recovered. The same double enzyme digestion was performed on a recombinant expression vector DBNBC-01, and a linearized plasmid was recovered and ligated with a target fragment, thereby obtaining a recombinant expression vector DBNBC-01-r1. The recombinant expression vector DBNBC-01-r1 was double digested with Xho I and Sac I, and a linearized plasmid was recovered. A recombinant cloning vector containing the antisense strand was double digested with Xho I and Sac I, and an antisense strand fragment was recovered. The double digested recombinant expression vector DBNBC-01-r1 was ligated with the antisense strand fragment, thereby obtaining a recombinant expression vector DBNBC-01-r1X2. The recombinant expression vector DBNBC-01-r1X2 and puc-Spacer with a spacer sequence were double digested with Hind III and Sac I, respectively, and the spacer sequence and linearized DBNBC-01-r1X2 were recovered and ligated, so as to construct a recombinant expression vector DBN100462 containing a cauliflower mosaic virus 35S promoter-sense strand of the target sequence-spacer sequence-antisense strand of the target sequence. Constructing a vector using a conventional enzyme digestion method is well known to a person skilled in the art, and the vector schematic diagram of the recombinant expression vector DBN100462 is shown as in FIG. 1 (Kan: kanamycin gene; RB: the right boundary; prCaMV35S: cauliflower mosaic virus 35S (SEQ ID NO: 7); r1 (SEQ ID NO: 4): the nucleotide sequence of target sequence 1 (SEQ ID NO: 1)+spacer sequence+the reverse complementary nucleotide sequence of target sequence 1; tNos: the terminator of nopaline synthase gene (SEQ ID NO: 8); Hpt: hygromycin phosphotransferase gene (SEQ ID NO:9); and LB: the left boundary).

*Escherichia coli* T1 competent cells were transformed with the recombinant expression vector DBN100462 by a heat shock method with the following heat shock conditions: water bathing 50 μl of *Escherichia coli* T1 competent cells and 10 μl of plasmid DNA (recombinant expression vector DBN100462) at 42° C. for 30 seconds; shake culturing at 37° C. for 1 hour (using a shaker at a rotation speed of 100 rpm for shaking); then culturing under the condition of a temperature of 37° C. on an LB solid plate containing 50 mg/L of kanamycin (10 g/L of tryptone, 5 g/L of yeast extract, 10 g/L of NaCl, and 15 g/L of agar, adjusted to a pH of 7.5 with NaOH) for 12 hours, picking white colonies, and culturing under the conditions of a temperature of 37° C. overnight in an LB liquid culture medium (10 g/L of tryptone, 5 g/L of yeast extract, 10 g/L of NaCl, and 50 mg/L of kanamycin, adjusted to a pH of 7.5 with NaOH). The plasmids in the cells were extracted through an alkaline method. The extracted plasmids were sequenced and identified through PCR, and the results demonstrated that the recombinant expression vector DBN100462 was correctly constructed.

According to the above-mentioned method, recombinant expression vectors DBN100460 and DBN100463 were constructed, *Escherichia coli* T1 competent cells were transformed with the recombinant expression vectors DBN100460 and DBN100463 by a heat shock method, and the plasmids in the cells were extracted through an alkaline method. The plasmids were identified through PCR, and the PCR products were sequenced and identified, thereby determining that the recombinant expression vectors DBNBC100460 and DBNBC100463 were constructed correctly.

Example 3. Transformation of *Agrobacterium* with the Recombinant Expression Vectors

*Agrobacterium* LBA4404 (Invitrogen, Chicago, USA, CAT: 18313-015) was transformed with the recombinant expression vectors DBN100462, DBN100460 and DBN100463 which had been correctly constructed using a liquid nitrogen method, with the following transformation conditions: placing 100 μL of *Agrobacterium* LBA4404, and 3 μL of plasmid DNA (recombinant expression vector) in liquid nitrogen for 10 minutes, and warm water bathing at 37° C. for 10 minutes; inoculating the transformed *Agrobacterium* LBA4404 into an LB tube, culturing under the conditions of a temperature of 28° C. and a rotation speed of 200 rpm for 2 hours, and then spreading on an LB plate containing 50 mg/L of rifampicin and 100 mg/L of kanamycin until positive single clones were grown, picking out single clones for culturing and extracting the plasmids thereof, and performing verification by enzyme digestion on the recombinant expression vectors DBN100462, DBN100460 and DBN100463 with restriction endonucleases EcoR I and Xho I, with the results demonstrating that the structures of the recombinant expression vectors DBN100462, DBN100460 and DBN100463 were completely correct.

Example 4. Acquisition of Transgenic Maize Plants

According to the conventionally used *Agrobacterium* infection method, young embryos of maize variety Zong31 (Z31) cultured under sterile conditions were co-cultured with the *Agrobacterium* in Example 3, so as to transfer T-DNA (comprising the r1 nucleotide sequence, r2 nucleotide sequence, r3 nucleotide sequence, a promoter sequence of a cauliflower mosaic virus 35S gene, a Hpt gene and a Nos terminator sequence) in the recombinant expression vectors DBN100462, DBN100460 and DBN100463 constructed in Example 2 into the maize chromosome, thereby obtaining maize plants with the r1 nucleotide sequence incorporated, maize plants with the r2 nucleotide sequence incorporated, and maize plants with the r3 nucleotide sequence incorporated respectively; meanwhile, wild type maize plants were used as the control.

As regards the *Agrobacterium*-mediated maize transformation, briefly, immature young embryos were separated from maize, and contacted with an *Agrobacterium* suspension, wherein the *Agrobacterium* can transfer the r1 nucleotide sequence, the r2 nucleotide sequence, and the r3 nucleotide sequence to at least one cell of one of the young embryos (step 1: the infection step). In this step, the young embryos were preferably immersed in an *Agrobacterium* suspension ($OD_{660}$=0.4-0.6, a culture medium for infection (4.3 g/L of MS salt, MS vitamin, 300 mg/L of casein, 68.5 g/L of sucrose, 36 g/L of glucose, 40 mg/L of acetosyringone (AS), and 1 mg/L of 2,4-dichlorphenoxyacetic acid (2,4-D), pH 5.3)) to initiate the inoculation. The young embryos were co-cultured with *Agrobacterium* for a period of time (3 days) (step 2: the co-culturing step). Preferably, the young embryos were cultured in a solid culture medium (4.3 g/L of MS salt, MS vitamins, 300 mg/L of casein, 20 g/L of sucrose, 10 g/L of glucose, 100 mg/L of acetosyringone (AS), 1 mg/L of 2,4-dichlorphenoxyacetic acid (2,4-D), and 8 g/L of agar, pH 5.8) after the infection step. After this co-culturing stage, there can be an optional "recovery" step. In the "recovery" step, there may be at least one antibiotic (cephalosporin) known to inhibit the growth of *Agrobacterium* in a culture medium for recovery (4.3 g/L of MS salt, MS vitamin, 300 mg/L of casein, 30 g/L of sucrose, 1 mg/L of 2,4-dichlorphenoxyacetic acid (2,4-D), and 3 g/L of phytagel, with a pH of 5.8), without the addition of a selective agent for plant transformant (step 3: the recovery step). Preferably, the young embryos were cultured in a solid culture medium with the antibiotic, but without the selective agent, to eliminate *Agrobacterium* and provide a recovery stage for the infected cells. Subsequently, the inoculated young embryos were cultured in a culture medium containing a selective agent (hygromycin), and growing transformed calli were selected (step 4: the selection step). Preferably, the young embryos were cultured in a solid culture medium for selection (4.3 g/L of MS salt, MS vitamin, 300 mg/L of casein, 30 g/L of sucrose, 50 mg/L of hygromycin, 1 mg/L of 2,4-dichlorphenoxyacetic acid (2,4-D), and 3 g/L of phytagel, with a pH of 5.8) with the selective agent, resulting in selective growth of transformed cells. Then, plants were regenerated from the calli (step 5: the regeneration step). Preferably, the calli grown on a culture medium containing the selective agent were cultured in solid culture media (an MS differentiation culture medium and MS rooting culture medium) to regenerate plants.

Resistant calli which were screened out were transferred onto the MS differentiation culture medium (4.3 g/L of MS salt, MS vitamin, 300 mg/L of casein, 30 g/L of sucrose, 2 mg/L of 6-benzyladenine, 50 mg/L of hygromycin, and 3 g/L of phytagel, with a pH of 5.8), and cultured at 25° C. for differentiation. The differentiated seedlings were transferred onto the MS rooting culture medium (2.15 g/L of MS salt, MS vitamin, 300 mg/L of casein, 30 g/L of sucrose, 1 mg/L of indole-3-acetic acid, and 3 g/L of phytagel, with a pH of 5.8), cultured at 25° C. until reaching a height of about 10 cm, and transferred to a greenhouse for culturing until fruiting. In the greenhouse, the plants were cultured at 28° C. for 16 hours, and then cultured at 20° C. for 8 hours every day.

Example 5. Acquisition of Transgenic Soybean Plants

According to the conventionally used *Agrobacterium* infection method, cotyledonary node tissues of soybean variety Zhonghuang13 cultured under sterile conditions were co-cultured with the *Agrobacterium* in Example 3, so as to transfer T-DNA (comprising the r1 nucleotide sequence, r2 nucleotide sequence, r3 nucleotide sequence, a promoter sequence of a cauliflower mosaic virus 35S gene, a Hpt gene and a Nos terminator sequence) in the recombinant expression vectors DBN100462, DBN100460 and DBN100463 constructed in Example 2 into the soybean chromosome, thereby obtaining soybean plants with the r1 nucleotide sequence incorporated, soybean plants with the r2 nucleotide sequence incorporated, and soybean plants with the r3 nucleotide sequence incorporated respectively; meanwhile, wild type soybean plants were used as the control.

As regards the *Agrobacterium*-mediated soybean transformation, briefly, mature soybean seeds were germinated in a culture medium for soybean germination (3.1 g/L of B5 salt, B5 vitamin, 20 g/L of sucrose, and 8 g/L of agar, with a pH of 5.6), and the seeds were inoculated on the culture medium for germination and cultured under the conditions of a temperature of 25±1° C.; and a photoperiod (light/dark) of 16 h/8 h. After 4-6 days of germination, soybean sterile seedlings swelling at bright green cotyledonary nodes were taken, hypocotyls were cut off 3-4 millimeters below the cotyledonary nodes, the cotyledons were cut longitudinally, and apical buds, lateral buds and seminal roots were removed. A wound was made at a cotyledonary node using the knife back of a scalpel, the wounded cotyledonary node tissues were contacted with an *Agrobacterium* suspension, wherein the *Agrobacterium* can transfer the r1 nucleotide sequence, the r2 nucleotide sequence and the r3 nucleotide sequence to the wounded cotyledonary node tissues (step 1: the infection step). In this step, the cotyledonary node tissues were preferably immersed in the *Agrobacterium* suspension ($OD_{660}$=0.5-0.8, a culture medium for infection (2.15 g/L of MS salt, B5 vitamin, 20 g/L of sucrose, 10 g/L of glucose, 40 mg/L of acetosyringone (AS), 4 g/L of 2-morpholine ethanesulfonic acid (MES), and 2 mg/L of zeatin (ZT), with a pH of 5.3)) to initiate the inoculation. The cotyledonary node tissues were co-cultured with the *Agrobacterium* for a period of time (3 days) (step 2: the co-culturing step). Preferably, the cotyledonary node tissues were cultured in a solid culture medium (4.3 g/L of MS salt, B5 vitamin, 20 g/L of sucrose, 10 g/L of glucose, 4 g/L of 2-morpholine ethanesulfonic acid (MES), 2 mg/L of zeatin, and 8 g/L of agar, with a pH of 5.6) after the infection step. After this co-culturing stage, there can be an optional "recovery" step. In the "recovery" step, there may be at least one antibiotic (cephalosporin) known to inhibit the growth of *Agrobacterium* in a culture medium for recovery (3.1 g/L of B5 salt, B5 vitamin, 1 g/L of 2-morpholine ethanesulfonic acid (MES), 30 g/L of sucrose, 2 mg/L of zeatin (ZT), 8 g/L of agar, 150 mg/L of cephalosporin, 100 mg/L of glutamic acid, and 100 mg/L of aspartic acid, with a pH of 5.6), without the addition of a selective agent for plant transformant (step 3: the recovery step). Preferably, tissue blocks regenerated from the cotyledonary nodes were cultured in a solid culture medium with the antibiotic, but without the selective agent, to eliminate *Agrobacterium* and provide a recovery stage for the infected cells. Subsequently, the tissue blocks regenerated from the cotyledonary nodes were cultured in a culture medium containing a selective agent (hygromycin), and growing transformed calli were selected (step 4: the selection step). Preferably, the tissue blocks regenerated from the cotyledonary nodes were cultured in a solid culture medium for selection (3.1 g/L of B5 salt, B5 vitamin, 1 g/L of 2-morpholine ethanesulfonic acid (MES), 30 g/L of sucrose, 1 mg/L of 6-benzyladenine (6-BAP), 8 g/L of agar, 150 mg/L of cephalosporin, 100 mg/L of glutamic acid, 100 mg/L of aspartic acid, and 50 mg/L of hygromycin, with a pH of 5.6) with the selective agent, resulting in selective growth of transformed cells. Then, plants were regenerated from the transformed cells (step 5: the regeneration step). Preferably, the tissue blocks regenerated from the cotyledonary nodes grown on a culture medium containing the selective agent were cultured in solid culture media (B5 differentiation culture medium and B5 rooting culture medium) to regenerate plants.

The screened out resistant tissues were transferred onto the B5 differentiation culture medium (3.1 g/L of B5 salt, B5 vitamin, 1 g/L of 2-morpholine ethanesulfonic acid (MES), 30 g/L of sucrose, 1 mg/L of zeatin (ZT), 8 g/L of agar, 150 mg/L of cephalosporin, 50 mg/L of glutamic acid, 50 mg/L of aspartic acid, 1 mg/L of gibberellin, 1 mg/L of auxin, and 50 mg/L of hygromycin, with a pH of 5.6), and cultured at 25° C. for differentiation. The differentiated seedlings were transferred onto the B5 rooting culture medium (3.1 g/L of B5 salt, B5 vitamin, 1 g/L of 2-morpholine ethanesulfonic acid (MES), 30 g/L of sucrose, 8 g/L of agar, 150 mg/L of cephalosporin, and 1 mg/L of indole-3-butyric acid (IBA)), cultured in the rooting culture medium at 25° C. until reaching a height of about 10 cm, and transferred to a greenhouse for culturing until fruiting. In the greenhouse, the plants were cultured at 26° C. for 16 hours, and then cultured at 20° C. for 8 hours every day.

Example 6. Acquisition of Transgenic Cotton Plants

According to the conventionally used *Agrobacterium* infection method, hypocotyl tissues of cotton variety Coker312 cultured under sterile conditions were co-cultured with the *Agrobacterium* in Example 3, so as to transfer T-DNA (comprising the r1 nucleotide sequence, r2 nucleotide sequence, r3 nucleotide sequence, a promoter sequence of a cauliflower mosaic virus 35S gene, a Hpt gene and a Nos terminator sequence) in the recombinant expression vectors DBN100462, DBN100460 and DBN100463 constructed in Example 2 into the cotton chromosome, thereby obtaining cotton plants with the r1 nucleotide sequence incorporated, cotton plants with the r2 nucleotide sequence incorporated, and cotton plants with the r3 nucleotide sequence incorporated respectively; meanwhile, wild type cotton plants were used as the control.

As regards the *Agrobacterium*-mediated cotton transformation, briefly, seed coats of sulfuric acid delinted seeds were peeled off and the peeled seeds were immersed in 0.1% of a mercuric chloride solution for 15 min, washed and cleaned with sterile water, planted on a sterile culture medium for seedling germination (½ MS macro-elements (Murashige and Skoog, 1962) supplemented with 15 g/L of glucose and 2.5 g/L of phytagel (Sigma, USA)), cultured in the dark for 3 days, placed in a culture chamber, and cultured for 2 days for use. Hypocotyls of sterile seedlings were taken and cut into small segments of around 0.5 cm, inoculated onto a culture medium for callus induction (MSB+0.1 mg/L of 2,4-D+0.1 mg/L of KT) for inducing calli, and after about 25 days, subcultured once with the same culture medium. Healthy embryonic calli with a uniform texture which had been pre-cultured for 15 days were taken as transformation explants, the embryonic calli were inoculated in a 100 ml conical flask into which an *Agrobacterium* suspension was added (OD660=around 0.5), and immersed for 10 min, in which the *Agrobacterium* suspension was contacted with calli, and the *Agrobacterium* can transfer the r1 nucleotide sequence, the r2 nucleotide sequence and the r3 nucleotide sequence to at least one cell of the calli. The calli were placed on sterile filter paper so that the bacterial liquid on surface was absorbed, inoculated onto a co-culture medium (MSB+0.1 mg/L of 2,4-D+0.1 mg/L of KT+50 mg/L of AS+3% glucose+0.25% phytagel, with a pH of 5.6), and cultured in the dark for 48 h. The co-cultured calli were firstly washed twice by quickly shaking with sterile water, then immersed in sterile water for 10 min and immersed in sterile water into which 600 mg/L of Cef was added for 15 min, the bacterial liquid was poured off, and the calli were placed on sterile filter paper for drying, and then inoculated onto a culture medium for selection (MSB+0.1 mg/L of 2,4-D+0.1 mg/L of KT+3% glucose+0.3% phytagel, 50 mg/L of kanamycin and 400 mg/L of cephalosporin, with a pH of 5.9), and cultured at 28° C. under weak light. The resistant callus tissues from the culture medium for selection were inoculated onto a differentiation culture medium (an MSB basis culture media ($KNO_3$ doubled, with $NH_4NO_3$ removed, and 2.0 g/L of Gln and 1.0 g/L of Asn added)), and differentiated mature cotyledon embryos were inoculated onto a low salt culture medium for seedling development (½ MS inorganic salts+B5 organics, with 15 g/L of glucose and 2.5 g/L of phytagel added) for germination and seedling development. The regenerated tube seedlings were cut into wedge shapes (a length of about 1 cm), inserted into pre-prepared stocks, with the grafting sites being bound tightly with parafilm films, and then moisturized in a culture chamber, and can be directly transplanted to a greenhouse after 2-3 pieces of new leaves were germinated from the scions.

Example 7. Verification of the Transgenic Maize Plants, the Transgenic Soybean Plants and the Transgenic Cotton Plants Using TaqMan Leaves of about 100 mg from the maize plants into which the r1 nucleotide sequence, the r2 nucleotide sequence or the r3 nucleotide sequence was incorporated, were taken as samples. The genomic DNA thereof was extracted with a DNeasy Plant Maxi Kit of Qiagen respectively, and the copy number of a Hpt gene was detected by the Taqman probe fluorescence quantitative PCR method so as to determine the copy numbers of the r1 nucleotide sequence, the r2 nucleotide sequence and the r3 nucleotide sequence. Meanwhile, wild type maize plants were used as the control, and detected and analyzed according to the above-mentioned method. Triple repeats were set for the experiments, and were averaged.

The particular method for detecting the copy number of the Hpt gene was as follows:

Step 701. Leaves of 100 mg from the maize plants into which the r1 nucleotide sequence, the r2 nucleotide sequence or the r3 nucleotide sequence was incorporated and wild type maize plants were respectively taken, ground into a homogenate in a mortar with liquid nitrogen, and triple repeats were taken for each sample;

Step 702. The genomic DNA of the above-mentioned samples was extracted using a DNeasy Plant Mini Kit of Qiagen, and the particular method can refer to the product manual thereof;

Step 703. The concentrations of the genomic DNAs of the above-mentioned samples were detected using NanoDrop 2000 (Thermo Scientific);

Step 704. The concentrations of the genomic DNAs of the above-mentioned samples were adjusted to a consistent concentration value which ranges from 80 to 100 ng/μL;

Step 705. The copy numbers of the samples were identified using the Taqman probe fluorescence quantitative PCR method, wherein samples for which the copy numbers had been identified and known were taken as standards, the samples of the wild type maize plants were taken as the control, and triple repeats were taken for each sample, and were averaged; the sequences of the primers and probe for fluorescence quantitative PCR were as follows, respectively: The following primers and probe were used for detecting the Hpt nucleotide sequence:

Primer 1: CAGGGTGTCACGTTGCAAGA as shown in SEQ ID NO: 10 of the sequence listing;

Primer 2: CCGCTCGTCTGGCTAAGATC as shown in SEQ ID NO: 11 of the sequence listing;

Probe 1: TGCCTGAAACCGAACTGCCCGCTG as shown in SEQ ID NO: 12 of the sequence listing;

PCR Reaction System:

| | |
|---|---|
| JumpStart ™ Taq ReadyMix ™ (Sigma) | 10 μl |
| 50× primer/probe mixture | 1 μl |
| genomic DNA | 3 μl |
| water (dd$H_2O$) | 6 μl |

The 50× primer/probe mixture comprises 45 μl of each primer at a concentration of 1 mM, 50 μl of the probe at a concentration of 100 μM, and 860 μl of 1×TE buffer, and was stored at 4° C. in an amber tube.

PCR Reaction Conditions:

| Step | Temperature | Time |
|---|---|---|
| 711 | 95° C. | 5 minutes |
| 712 | 95° C. | 30 seconds |
| 713 | 60° C. | 1 minute |
| 714 | back to step 712, repeated 40 times | |

Data was analyzed using software SDS2. 3 (Applied Biosystems).

By analyzing the experimental results of the copy number of the Hpt gene, it was further demonstrated whether the r1 nucleotide sequence, the r2 nucleotide sequence and the r3 nucleotide sequence were all incorporated into the chromosome of the detected maize plants, and whether all of the maize plants into which the r1 nucleotide sequence, the r2 nucleotide sequence or the r3 nucleotide sequence was incorporated resulted in single-copy transgenic maize plants.

According to the above-mentioned method of verifying the transgenic maize plants using TaqMan, the transgenic soybean plants and the transgenic cotton plants were detected and analyzed. It was further demonstrated, by analyzing the experimental results of the copy number of the Hpt gene, that the r1 nucleotide sequence, the r2 nucleotide sequence and the r3 nucleotide sequence were all respectively incorporated into the chromosomes of the detected soybean and cotton plants, and all of the soybean plants into which the r1 nucleotide sequence, the r2 nucleotide sequence or the r3 nucleotide sequence was incorporated, and the cotton plants into which the r1 nucleotide sequence, the r2 nucleotide sequence or the r3 nucleotide sequence was incorporated resulted in single-copy transgenic plants.

Example 8. Synthesis of dsRNA

Three target sequences obtained from Example 1 were cleaved off from a pMD18-T vector (Takara Co.), and ligated to an engineered L4440 plasmid, thus obtaining the dsRNA which can be used for bioassays. The particular construction method was as follows:

synthesizing the primer sequences for dsRNA, in which sense strand F was: TCGGGATCCXXXXXXXXXX; and sense strand R was: GACAAGCTTXXXXXXXXXX; wherein TCG/GAC was a protective site, underlined sequences were restriction enzyme sites of BamH I/Hind III for the sense strand, and Nde I/Xba I for the antisense strand, respectively; XXX represented primer sequences for different genes, the antisense strand was a reverse complementary sequence of the sense strand, and reference was made to Table 2.

TABLE 2

Information on primers for synthesizing the dsRNA sequence

| Sequence number | Primer name | Primer sequence 5'-3' |
|---|---|---|
| SEQ ID NO: 13 | Target sequence 1-F | AAGCAAATAGTAGTAGAC |
| SEQ ID NO: 14 | Target sequence 1-R | GTTTCCAAAGGCAACCGG |
| SEQ ID NO: 15 | Target sequence 2-F | TTGAAGCCGAAATGATGA |
| SEQ ID NO: 16 | Target sequence 2-R | GTTTCCAAAGGCAACCGG |
| SEQ ID NO: 17 | Target sequence 3-F | GTCACGCTCCGCATCAGA |
| SEQ ID NO: 18 | Target sequence 3-R | TGAGCGATCAAGTCGAGA |

PCR amplification of the sense strand was respectively performed using Lygus cDNA as the template, for obtaining a PCR product, with the following amplification conditions: 95° C. for 3 min, 94° C. for 30 s, 55° C. for 30 s, 72° C. for 30 s, and 72° C. for 10 min, and the PCR product was detected with agarose electrophoresis at a mass concentration of 1%.

The obtained PCR product was ligated to the engineered L4440 plasmid. The ligated product was transformed into HT115 (DE3) (purchased from addgene Co.) competent cells (this strain was a deficient Escherichia coli strain having the following sites: F-, mcrA, mcrB, IN (rrnDrrnE) 1, rnc14::Tn10 (DE3) lysogen:lavUV5 promoter-T7 polymerase). Under the induction of tetracycline, the deletion of RNase III gene was caused by the impact of Tn10 transposon, and under the induction of IPTG, HT115 can specifically express a T7 polymerase which recognizes the T7 primer sequence at the insertion site so that dsRNA was produced through folding; and positive clones were screened through the blue-white spot screening.

Single clones were picked out and transferred to an LB liquid culture medium containing 100 μg/ml of ampicillin and 12.5 μg/ml of tetracycline, and cultured at 37° C. for 10-14 h.

The culture liquid was diluted 100 times, and added to a 2×YT culture medium (16 g of peptone, 10 g of yeast extract, and 4 g of sodium chloride, dissolved in 1 L water, with a pH of 7.0), and when $OD_{595}$ reached 0.4, 0.4 mM of IPTG was added, and then incubated at 37° C. with shaking for 4 h, to thereby obtain the dsRNA expression products of the gene. (Referring to Ravi S Kamath, Maruxa Martinez-Campos, PederZipper len, Anderw G Fraser, J. Ahringer- Effectiveness of specific RNA-mediated interference through ingested double-stranded RNA in Caenorhabditis elegans, Genome Biol. 2, 0002.1 (2000)).

The obtained bacteria can be directly used for pesticide application; and it is also possible that the recombinant plasmid can be purified to isolate dsRNA for pesticide application.

Example 9. Purification of dsRNA

The expression product containing dsRNA obtained according to Example 8 was purified, and the particular method for purifying the recombinant plasmid and isolating dsRNA was as follows:

Step 901. 2 ml of bacterial liquid was taken for a small plasmid extraction to demonstrate that the plasmid was effectively amplified; the remaining bacterial liquid was poured into a 50 ml centrifugal tube, and centrifuged at a temperature of 4° C. at 5500 rpm for 10 min; and the centrifugal tube was inverted to remove as much as possible of the remaining LB;

Step 902. 6.6 ml alkaline lysis liquid I (50 mmol/L of glucose, 25 mmol/L of Tris-HCl (pH 7.6), and 10 mmol/L of EDTA, dissolved in 1 L sterile water, followed by high temperature sterilization and adding 0.5 ml of 1% RNase) was added, and the bacteria were blown and sucked or re-suspended through Vortex; 1 ml of freshly formulated lysozyme of 10 mg/ml was added; 13.3 ml of freshly formulated alkaline lysis liquid II (0.2 N NaOH, and 1% SDS) was added and shaken slightly to mix same uniformly, and left at room temperature for 5-10 min; and 10 ml of ice pre-cooled alkaline lysis liquid III (5 mol/L of potassium acetate (60 ml), 11.5 ml of glacial acetic acid and 28.5 ml of water) was added, and fully inverted for mixing uniformly, and the centrifugal tube was placed on ice for 10 min;

Step 903. Centrifugation was performed at a temperature of 4° C. at 20000 g for 10 min; the supernatant was added to a new centrifugal tube, together with 0.6 volume of isopropanol by volume based on the volume of the supernatant (if the volume was too large, two tubes can be provided), mixed uniformly and adequately, and left at room temperature for 10 min; and centrifugation was performed at room temperature at 12000 g for 15 min;

Step 904. The supernatant was discarded, the tube wall was rinsed with 70% ethanol, the ethanol was poured off, followed by drying for 10-15 min with inversion; the precipitate was dissolved with 3 ml water; the nucleic acid solution was pre-cooled with ice to a temperature of 0° C.; and an equal volume (3 ml) of ice-cold LiCl of 5 mol/L was added, mixed uniformly, and centrifuged at a temperature of 4° C. at 12000 g for 10 min;

Step 905. The supernatant was transferred to a new centrifugal tube, an equal volume (6 ml) of isopropanol was added, mixed uniformly, and centrifuged at room temperature at 12000 g for 10 min;

Step 906. After pouring off the supernatant, the centrifugal tube was inverted so as to drain the liquid, the precipitate and tube wall were rinsed with ethanol at a mass fraction of 70% at room temperature, and the ethanol was drained by inversion so that the ethanol in the precipitate was volatilized;

Step 907. The nucleic acid precipitate was dissolved with 500 μl water containing RNaseA (20 μg/ml), and the solution was transferred to a 1.5 ml centrifugal tube, and digested at a temperature of 37° C. for 30 min;

Step 908. An equal volume (500 μl) of phenol and chloroform was added, mixed uniformly through Vortex, and centrifuged at the highest speed at a temperature of 4° C. for 2 min, and the supernatant was transferred to another centrifugal tube (if the protein membrane is too thick, this step can be repeated until the protein is eliminated);

Step 909. An equal volume (500 μl) of chloroform was added, mixed uniformly through Vortex to extract phenol, and centrifuged at the highest speed at a temperature of 4° C. for 2 min, and the supernatant was transferred to another centrifugal tube; 2 volumes of absolute ethanol (1 ml) were added (if the protein membrane is too thick, this step can be repeated until the protein is eliminated);

Step 910. 1 ml of ethanol at a mass fraction of 70% was added, washed by inverting several times, centrifuged at the highest speed at a temperature of 4° C. for 2 min, and the supernatant was aspirated, followed by inverting for 10-15 min so as to volatilize the ethanol;

Step 911. The plasmid precipitate was dissolved with 1 ml of water, and 0.5 ml of a PEG-MgCl$_2$ solution was added; and after mixing uniformly, being placed at room temperature for more than 10 min, and being centrifuged at the highest speed at room temperature for 20 min, the plasmid was recovered;

Step 912. The precipitate was resuspended with 0.5 ml of ethanol at a mass fraction of 70% to remove PEG, centrifuged at the highest speed at room temperature for 5 min, repeatedly washed once, and placed for 10-20 min after absorbing ethanol until dry so as to volatilize the ethanol;

Step 913. The wettish plasmid was dissolved with 200 μl ddH$_2$O or TE (pH 8.0), and stored at a temperature of −20° C.;

Step 914. The obtained plasmid was digested with enzymes BamH I/Hind III, thereby obtaining the specific dsRNA.

Example 10. Identification of Control Ability for Lygus by Spraying dsRNA

1. As described in Example 8, a dsRNA expression bacterial liquid was cultured at 37° C., and the bacterial liquid was cultured until OD600=around 2.0. When OD595 reached 0.4, 0.4 mM of IPTG was added, and incubation was performed at 37° C. with shaking until OD600=around 2.0.

2. The bacterial liquid was uniformly sprayed onto soybean leaves.

dsRNA was sprayed onto soybean leaves (0.1 ml/cm$^2$ soybean leaves), the leaves with dsRNA to be sprayed thereon were changed each day, the bacterial liquid not expressing the dsRNA was used as a blank control, 50 larvae were used as a treatment group, the insects were observed and recorded each day for the death rate and were fed for 1-7 days, and the statistical results were as shown in Table 2. An insecticidal effect produced by feeding the insects with the hosts expressing dsRNA was actually a feeding-based insecticidal effect resulting from the nucleic acid inhibition effect of target gene dsRNA expressed by the hosts.

TABLE 2

A death statistical table after the target sequence dsRNA was fed to larvae of Lygus

| Number | Gene name | Death rate of Lygus (%) |
|---|---|---|
| 1 | Target sequence 1 | 87 |
| 2 | Target sequence 2 | 82 |
| 3 | Target sequence 3 | 78 |
| 4 | CK | 18 |

Example 11. Identification of an Insecticidal Effect of Transgenic Maize on Lygus The insecticidal effect against Lygus of the maize plants into which the r1 nucleotide sequence, the r2 nucleotide sequence or the r3 nucleotide sequence was incorporated was detected.

Step 1101. Eight cases of DBN100462 maize transformation events (r1) with a positive single copy, eight cases of DBN100460 maize transformation events (r3) with a positive single copy, and eight cases of DBN100463 maize transformation events (r2) with a positive single copy, which were identified through Taqman, and three cases of maize transformation events (NGM1) which were identified as negative through Taqman were chosen, wherein three strains were chosen for each transformation event, with three seedlings being chosen for each strain; meanwhile, wild type maize plants were used as the control (CK1); and the plants were grown in a greenhouse until female ears sprouted out;

Step 1102. The materials in step 1101 were taken, and a small bunch of freshly grown filaments with a length of about 3 cm was taken from each seedling, and laid and placed in a culture dish with a moist filter paper laid thereon, so that the filaments would not overlap with each other to the greatest extent, so as to facilitate the later observation of the death rate;

Step 1103. 20 newly-incubated insects of Lygus with an incubation time of not more than 24 hours were placed in each dish, the covers of the dishes covered same tightly, the culture dishes were placed in a bioassay box with a moist piece of gauze laid at the bottom thereof, and the bioassay box was placed in a bioassay chamber at a temperature of 24±2° C., D/L of 24/0, and a humidity of 70%-80%;

Step 1104. Considering that the newly-incubated insects of Lygus are small and weak, and easily suffer from mechanical injuries, it was better to keep the culture dishes unmoved on the day that the insects were incubated and 1 day after incubating the insects;

Step 1105. Starting on day 2 after the incubation of the insects, surviving Lygus numbers were counted from the exterior of the culture dishes every day, three strains for each transformation event were taken for an average level, and eight transformation events for each vector were taken for an average survival number level; insects of Lygus surviving in the culture dishes were transferred to culture dishes charged with fresh filaments every three days, and the experimental results are as shown in Table 3.

TABLE 3

Experimental results of feeding Lygus with filaments having maize transformation events

| Material | Target sequence contained | Survival number of Lygus at each day after bioassay | | | | | |
|---|---|---|---|---|---|---|---|
| | | DAI 2 | DAI 3 | DAI 4 | DAI 5 | DAI 6 | DAI 7 |
| MZ-DBN100460 | r3 | 15.5 ± 2.1 | 14.5 ± 0.7 | 11.5 ± 2.1 | 10.5 ± 3.5 | 5 ± 1.4 | 3 ± 1.4 |
| MZ-DBN100462 | r1 | 11 ± 2.8 | 6.5 ± 0.7 | 5 ± 0 | 4 ± 1.4 | 2 ± 0 | 2 ± 0 |
| MZ-DBN100463 | r2 | 13.3 ± 1.5 | 8 ± 3.6 | 5 ± 2.7 | 3.3 ± 1.1 | 2.3 ± 1.5 | 1.7 ± 1.1 |

TABLE 3-continued

Experimental results of feeding Lygus with filaments having maize transformation events

| Material number | Target sequence contained | Survival number of Lygus at each day after bioassay | | | | | |
|---|---|---|---|---|---|---|---|
| | | DAI 2 | DAI 3 | DAI 4 | DAI 5 | DAI 6 | DAI 7 |
| NGM1 | / | 19.7 ± 0.6 | 18.7 ± 0.6 | 18.3 ± 1.2 | 17.7 ± 0.6 | 17.3 ± 0.6 | 17.3 ± 0.6 |
| CK1 | / | 20 ± 0 | 16.5 ± 0.7 | 14.5 ± 0.7 | 13 ± 1.4 | 14.5 ± 0.7 | 15.5 ± 0.7 |

The experimental results in Table 3 demonstrate that the maize plants into which the r1 nucleotide sequence, the r2 nucleotide sequence or the r3 nucleotide sequence was incorporated all had good inhibitory effects on Lygus, and after 7 days, the fatality rate of Lygus can reach up to around 90%.

The results suggested that, as compared with the wild type maize plants, the maize plants into which the r1 nucleotide sequence, the r2 nucleotide sequence or the r3 nucleotide sequence was incorporated can all result in the death of a large amount of newly-incubated larvae of Lygus, and produce a great inhibition on the development progresses of very few surviving larvae, and the filaments of the maize plants into which the r1 nucleotide sequence, the r2 nucleotide sequence or the r3 nucleotide sequence was incorporated were generally only slightly damaged.

Example 12. Identification of an Insecticidal Effect of Transgenic Soybean on Lygus The insecticidal effect against Lygus of the soybean plants into which the r1 nucleotide sequence, the r2 nucleotide sequence or the r3 nucleotide sequence was incorporated was detected.

Step 1201. Eight cases of DBN100462 soybean transformation events (r1) with a positive single copy, eight cases of DBN100460 soybean transformation events (r3) with a positive single copy, and eight cases of DBN100463 soybean transformation events (r2) with a positive single copy, which were identified through Taqman, and three cases of soybean transformation events (NGM2) which were identified as negative through Taqman were chosen, wherein three strains were chosen for each transformation event, with three seedlings being chosen for each strain; meanwhile, wild type soybean plants were used as the control (CK2); and the plants were grown in a greenhouse until three pieces of euphylla were grown;

Step 1202. The materials in step 1201 were taken, and a piece of euphylla with a size of about 2×2 cm was taken from each seedling, and laid and placed in a culture dish with a moist filter paper laid thereon;

Step 1203. 20 newly-incubated insects of Lygus with an incubation time of not more than 24 hours were placed in each dish, the covers of the dishes covered same tightly, the culture dishes were placed in a bioassay box with a moist gauze laid at the bottom thereof, and the bioassay box was placed in a bioassay chamber at a temperature of 24±2° C., D/L of 24/0, and a humidity of 70%-80%;

Step 1204. Considering that the newly-incubated insects of Lygus are small and weak and easily suffer from mechanical injuries, it was better to keep the culture dishes unmoved on the day that the insects were incubated and 1 day after incubating the insects;

Step 1205. Starting on day 2 after the incubation of the insects, surviving Lygus numbers were counted from the exterior of the culture dishes every day, three strains for each transformation event were taken for an average level, and eight transformation events for each vector were taken for an average survival number level; insects of Lygus surviving in the culture dishes were transferred to culture dishes charged with fresh euphylla every 3 days, and the experimental results are as shown in Table 4.

TABLE 4

Experimental results of feeding Lygus with euphylla having soybean transformation events

| Material number | Target sequence contained | Survival number of Lygus at each day after bioassay | | | | | |
|---|---|---|---|---|---|---|---|
| | | DAI 2 | DAI 3 | DAI 4 | DAI 5 | DAI 6 | DAI 7 |
| SY-DBN100460 | r3 | 16.9 ± 1.4 | 13.3 ± 1.3 | 9.7 ± 1.3 | 7.3 ± 1.5 | 3.9 ± 1.2 | 1.3 ± 0.9 |
| SY-DBN100462 | r1 | 16.4 ± 1.4 | 13.3 ± 1.5 | 8.8 ± 1.3 | 4.3 ± 1.2 | 1.0 ± 0.9 | 0.4 ± 0.6 |
| SY-DBN100463 | r2 | 17.1 ± 1.6 | 12.4 ± 1.3 | 7.5 ± 1.4 | 3.8 ± 0.9 | 0.9 ± 0.4 | 0.2 ± 0.2 |
| NGM2 | / | 17.0 ± 0.4 | 16.4 ± 1.3 | 16.3 ± 1.2 | 16.0 ± 1.1 | 15.6 ± 1.0 | 15.4 ± 0.9 |
| CK2 | / | 18.4 ± 1.2 | 18.0 ± 1.3 | 17.6 ± 0.4 | 17.6 ± 0.4 | 16.8 ± 1.2 | 16.4 ± 0.8 |

The experimental results in Table 4 demonstrate that the soybean plants into which the r1 nucleotide sequence, the r2 nucleotide sequence or the r3 nucleotide sequence was incorporated all had good inhibitory effects on Lygus, and after 7 days, the fatality rate of Lygus can reach up to not less than 90%.

Example 13. Identification of an Insecticidal Effect of Transgenic Cotton on Lygus The insecticidal effect against Lygus of the cotton plants into which the r1 nucleotide sequence, the r2 nucleotide sequence or the r3 nucleotide sequence was incorporated was detected.

Step 1301. Eight cases of DBN100462 cotton transformation events (r1) with a positive single copy, eight cases of DBN100460 cotton transformation events (r3) with a positive single copy, and eight cases of DBN100463 cotton transformation events (r2) with a positive single copy, which were identified through Taqman, and three cases of cotton transformation events (NGM3) which were identified as negative through Taqman were chosen, wherein three strains were chosen for each transformation event, with three seedlings being chosen for each strain; meanwhile, wild type cotton plants were used as the control (CK3); and the plants were grown in a greenhouse until three pieces of euphylla were grown;

Step 1302. The materials in step 1301 were taken, and a piece of euphylla with a size of about 2×2 cm was taken from each seedling, and laid and placed in a culture dish with a moist filter paper laid thereon;

Step 1303. 20 newly-incubated insects of *Lygus* with an incubation time of not more than 24 hours were placed in each dish, the covers of the dishes covered same tightly, the culture dishes were placed in a bioassay box with a moist gauze laid at the bottom thereof, and the bioassay box was placed in a bioassay chamber at a temperature of 24±2° C., D/L of 24/0, and a humidity of 70%-80%;

Step 1304. Considering that the newly-incubated insects of *Lygus* are small and weak and easily suffer from mechanical injuries, it was better to keep the culture dishes unmoved on the day that the insects were incubated and 1 day after incubating the insects;

Step 1305. Starting on day 2 after the incubation of the insects, surviving *Lygus* numbers were counted from the exterior of the culture dishes every day, three strains for each transformation event were taken for an average level, and eight transformation events for each vector were taken for an average survival number level; insects of *Lygus* surviving in the culture dishes were transferred to culture dishes charged with fresh euphylla every three days, and the experimental results are as shown in Table 5.

TABLE 5

Experimental results of feeding Lygus with euphylla having cotton transformation events

| Material number | Target sequence contained | Survival number of Lygus at each day after bioassay | | | | | |
|---|---|---|---|---|---|---|---|
| | | DAI 2 | DAI 3 | DAI 4 | DAI 5 | DAI 6 | DAI 7 |
| CT-DBN100460 | r3 | 18.5 ± 1.2 | 15.2 ± 0.9 | 9.1 ± 0.8 | 7.0 ± 1.1 | 3.4 ± 0.4 | 0.9 ± 0.2 |
| CT-DBN100462 | r1 | 17.1 ± 1.3 | 14.2 ± 1.4 | 7.4 ± 1.0 | 3.9 ± 1.0 | 0.9 ± 0.3 | 0.5 ± 0.4 |
| CT-DBN100463 | r2 | 18.1 ± 1.2 | 13.2 ± 1.1 | 7.2 ± 1.0 | 3.3 ± 0.8 | 0.8 ± 0.3 | 0.1 ± 0.2 |
| NGM3 | / | 18.0 ± 0.5 | 17.2 ± 1.0 | 16.8 ± 1.2 | 16.5 ± 1.2 | 16.3 ± 0.9 | 15.8 ± 1.1 |
| CK3 | / | 18.8 ± 1.1 | 18.4 ± 1.1 | 18.0 ± 0.5 | 17.6 ± 0.8 | 17.2 ± 1.0 | 16.8 ± 1.2 |

The experimental results in Table 5 demonstrated that the cotton plants into which the r1 nucleotide sequence, the r2 nucleotide sequence or the r3 nucleotide sequence was incorporated all had good inhibitory effects on *Lygus*, and after 7 days, the fatality rate of *Lygus* can reach up to around 95%.

Example 14. Composition

Formula of a carrier acceptable in agricultural pharmacology for dsRNA (1 L system): 50 mM of $NaHPO_4$, pH of 7.0, 10 mM of β-mercaptoethanol, 10 mM of EDTA, sodium hexadecylsulfonate at a mass fraction of 0.1%, and polyethylene glycol octyl phenyl ether at a mass fraction of 0.1%, supplemented with $H_2O$ up to 1 L.

The above-mentioned formula was a buffer formula, and it was only required for any purified dsRNA to be directly added to the buffer only if the final concentration met requirements, such as 50 mg/L. The formula can also be prepared into a concentrated preparation as desired.

In summary, the present invention discloses, for the first time, three target sequences for controlling an insect pest from *Hemiptera, Lygus*, and transgenic plants (maize, soybean and cotton) obtained using RNAi technology. The transgenic plants control the invasion of *Lygus* efficiently and specifically by introducing dsRNA sequences formed from the target sequences of *Lygus*, and *Lygus* can be prevented from producing resistance, with the advantages of good environment compatibility, convenience and low cost.

Finally, it should be stated that the above embodiments are merely used for illustrating, rather than limiting, the technical solution of the present invention; and although the present invention has been described in detail with reference to the preferred embodiments, a person skilled in the art should understand that modifications or equivalent substitutions may be made to the technical solution of the present invention without departing from the spirit and scope of the technical solution of the present invention.

The invention claimed is:

1. An isolated polynucleotide sequence encoding a double stranded ribonucleic acid, wherein the polynucleotide comprises:
   (i) the nucleotide sequence of SEQ ID NO: 1, 2 or 3;
   (ii) a spacer sequence; and
   (iii) the fully complementary sequence of the nucleotide sequence of (i).

2. The isolated polynucleotide sequence according to claim 1, wherein the isolated polynucleotide sequence is SEQ ID NO: 4, 5 or 6.

3. An expression cassette or recombinant vector, comprising the isolated polynucleotide sequence of claim 1 operably linked to a regulatory sequence.

4. An interfering ribonucleic acid sequence, wherein the interfering ribonucleic acid sequence acts to downregulate expression of at least one target sequence in an insect pest from *Hemiptera* after being ingested by the insect pest, and wherein: the interfering ribonucleic acid sequence comprises at least one silencing element, and the silencing element is a double-stranded RNA region comprising complementary strands being annealed, with one strand of the double-stranded RNA region comprising a nucleotide sequence that is completely complementary to the target sequence, and the target sequence is selected from SEQ ID NO: 1, 2 or 3.

5. The interfering ribonucleic acid sequence according to claim 4, wherein the interfering ribonucleic acid sequence comprises at least two silencing elements and each of the silencing elements comprises a different nucleotide sequence that is completely complementary to a different target sequence.

6. The interfering ribonucleic acid sequence according to claim 4, further comprising a spacer sequence.

7. A composition for controlling invasion of a *Lygus* insect, comprising at least one of the interfering ribonucleic acid sequence of claim 4 or a host cell expressing the interfering ribonucleic acid sequence, and at least one suitable carrier, excipient or diluent.

8. The composition according to claim 7, wherein the composition is a solid, a liquid or a gel.

9. The composition according to claim 7, further comprising at least one pesticide, wherein:
   the pesticide is a chemical pesticide, a potato tuber-specific protein, a *Bacillus thuringiensis* insecticidal protein, a *Xenorhabdus ehlersii* insecticidal protein, a *Photorhabdus* insecticidal protein, a *Bacillus laterosporus* insecticidal protein or a *Bacillus sphaericus* insecticidal protein.

10. A method for controlling invasion of a *Lygus* insect comprising a step of contacting the *Lygus* insect with an effective amount of the interfering ribonucleic acid sequence of claim 4 or a composition comprising the interfering ribonucleic acid sequence.

11. A method for protecting a plant from damage caused by a *Lygus* insect, the method comprising a step of introducing the isolated polynucleotide sequence of claim 1, or an expression cassette comprising the isolated polynucleotide sequence under regulation of an operably linked regulatory sequence, or a recombinant vector comprising the isolated polynucleotide sequence into the plant, wherein when ingested by the *Lygus* insect, the plant being introduced inhibits growth of the *Lygus* insect.

12. A plant cell, plant protoplast, plant tissue culture, plant callus, plant or bacterium capable of controlling a *Lygus* insect, wherein the plant cell, plant protoplast, plant tissue culture, plant callus, plant or bacterium comprises the isolated polynucleotide sequence of claim 1, or an expression cassette comprising the isolated polynucleotide sequence under regulation of an operably linked regulatory sequence, or a recombinant vector comprising the isolated polynucleotide sequence.

13. The plant cell, plant protoplast, plant tissue culture, plant callus, plant or bacterium capable of controlling *Lygus* according to claim 12, wherein:
   the plant is soybean, wheat, barley, maize, tobacco, rice, rape, cotton or sunflower, and
   the plant tissue is an embryo, pollen, ovule, seed, leaf, flower, branch, fruit, kernel, ear, cob, husk, stalk, root, or root tip.

14. The interfering ribonucleic acid sequence according to claim 4, wherein the interfering ribonucleic acid sequence is SEQ ID NO: 4, 5 or 6.

15. The composition according to claim 7, wherein the host cell is a bacterial cell.

16. The composition according to claim 8, wherein the composition is an insecticidal spray.

17. The method according to claim 11, wherein:
   the plant is soybean, wheat, barley, maize, tobacco, rice, rape, cotton or sunflower.

* * * * *